US011248994B2

(12) United States Patent
Chou et al.

(10) Patent No.: US 11,248,994 B2
(45) Date of Patent: Feb. 15, 2022

(54) OPTICAL ADAPTER WITH A CARD SLOT FOR IMAGING A THIN SAMPLE LAYER

(71) Applicant: Essenlix Corporation, Monmouth Junction, NJ (US)

(72) Inventors: Stephen Chou, Princeton, NJ (US); Wei Ding, Princeton, NJ (US); Ji Qi, Hillsborough, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 0 days.

(21) Appl. No.: 17/268,729

(22) PCT Filed: Aug. 16, 2019

(86) PCT No.: PCT/US2019/046970
§ 371 (c)(1),
(2) Date: Feb. 16, 2021

(87) PCT Pub. No.: WO2020/037305
PCT Pub. Date: Feb. 20, 2020

(65) Prior Publication Data
US 2021/0247276 A1    Aug. 12, 2021

Related U.S. Application Data

(60) Provisional application No. 62/764,887, filed on Aug. 16, 2018, provisional application No. 62/719,201, filed on Aug. 17, 2018.

(51) Int. Cl.
*G01N 1/28* (2006.01)
*G01N 33/49* (2006.01)
*G01N 1/31* (2006.01)
*G02B 17/00* (2006.01)
*G01N 15/00* (2006.01)

(52) U.S. Cl.
CPC .......... *G01N 1/2813* (2013.01); *G01N 1/312* (2013.01); *G01N 33/492* (2013.01); *G02B 17/006* (2013.01); *G01N 2015/008* (2013.01); *G01N 2015/0073* (2013.01); *G01N 2015/0084* (2013.01)

(58) Field of Classification Search
CPC .... G01N 1/2813; G01N 33/492; G01N 1/312; G01N 15/1463; G01N 2015/1465; G01N 2015/0084; G01N 2015/0073; G01N 2015/008; G01N 33/49; G06K 9/0014; G06K 9/2018; G02B 17/006; B01L 3/50
See application file for complete search history.

(56) References Cited

U.S. PATENT DOCUMENTS

2005/0105077 A1\*  5/2005  Padmanabhan .. A61B 5/150221
                                                                356/39
2013/0316363 A1   11/2013  Wainwright et al.
(Continued)

FOREIGN PATENT DOCUMENTS

WO    2018148461 A1    8/2018

OTHER PUBLICATIONS

Written Opinion of the International Searching Authority for PCT/US2019/046970 established by the ISA/US completed on Dec. 18, 2019.

*Primary Examiner* — Michael P LaPage

(57) ABSTRACT

Disclosed are devices and methods for analyzing an analyte, such as white blood cells in liquid samples.

30 Claims, 10 Drawing Sheets

(56) References Cited

U.S. PATENT DOCUMENTS

| | | |
|---|---|---|
| 2014/0273076 A1 | 9/2014 | Adams et al. |
| 2015/0036131 A1* | 2/2015 | Salsman .............. G02B 21/365 |
| | | 356/244 |
| 2016/0004057 A1 | 1/2016 | Lin et al. |
| 2017/0189906 A1 | 7/2017 | Moll et al. |
| 2018/0066300 A1* | 3/2018 | Williams ................ C12Q 1/04 |
| 2018/0156775 A1 | 6/2018 | Chou et al. |
| 2018/0202903 A1 | 7/2018 | Chou et al. |
| 2020/0410205 A1* | 12/2020 | Echigo .................. G06T 3/0068 |

* cited by examiner

A

B

OPTICAL ADAPTER WITH A CARD SLOT FOR IMAGING A THIN SAMPLE LAYER

CROSS-REFERENCE TO RELATED APPLICATIONS

This application is a National Stage entry (§ 371) application of International Application No. PCT/US2019/046970, filed on Aug. 16, 2019, which claims the benefit of priority of U.S. Provisional Patent Application No. 62/764,887, filed on Aug. 16, 2018, and U.S. Provisional Patent Application No. 62/719,201, filed on Aug. 17, 2018, the contents of which are relied upon and incorporated herein by reference in their entirety. The entire disclosure of any publication or patent document mentioned herein is entirely incorporated by reference.

FIELD

Among other things, the present invention is related to devices and methods of performing biological and chemical assays, such as but not limited to assay related to analysis of white blood cells.

BACKGROUND

In biological and chemical assays (e.g. diagnostic testing), it is often necessary to measure and/or detect analytes of a sample or a part of the sample, quickly and simply. The current invention provides devices and methods for achieving these goals.

BRIEF DESCRIPTION OF THE DRAWINGS

The skilled artisan will understand that the drawings, described below, are for illustration purposes only. The drawings are not intended to limit the scope of the present teachings in any way. In some Figures, the drawings are in scale. In the figures that present experimental data points, the lines that connect the data points are for guiding a viewing of the data only and have no other means.

DETAILED DESCRIPTION OF EXEMPLARY EMBODIMENTS

The following detailed description illustrates some embodiments of the invention by way of example and not by way of limitation. The section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

Among other things, the present invention provides devices, systems, and methods of performing biological and chemical assays using a QMAX card.

The exemplary embodiments herein disclosed can be combined with the bio/chemical devices and assays including, but not limited to, the devices and assays as disclosed, described, and/or referred to in the following application: PCT/US2016/046437, which is hereby incorporated by reference in its entirety.

The embodiments in these applications herein incorporated can be regarded in combination with one another or as a single invention, rather than as discrete and independent filings.

Moreover, the exemplary embodiments disclosed herein are applicable to embodiments including but not limited to: bio/chemical assays, QMAX cards and systems, QMAX with hinges, notches, recessed edges and sliders, assays and devices with uniform sample thickness, smartphone detection systems, cloud computing designs, various detection methods, labels, capture agents and detection agents, analytes, diseases, applications, and samples; the various embodiments are disclosed, described, and/or referred to in the aforementioned applications, all of which are hereby incorporated in reference by their entireties.

Examples of QMAX Device with Hinges (QMAX Card)

Figure 1:
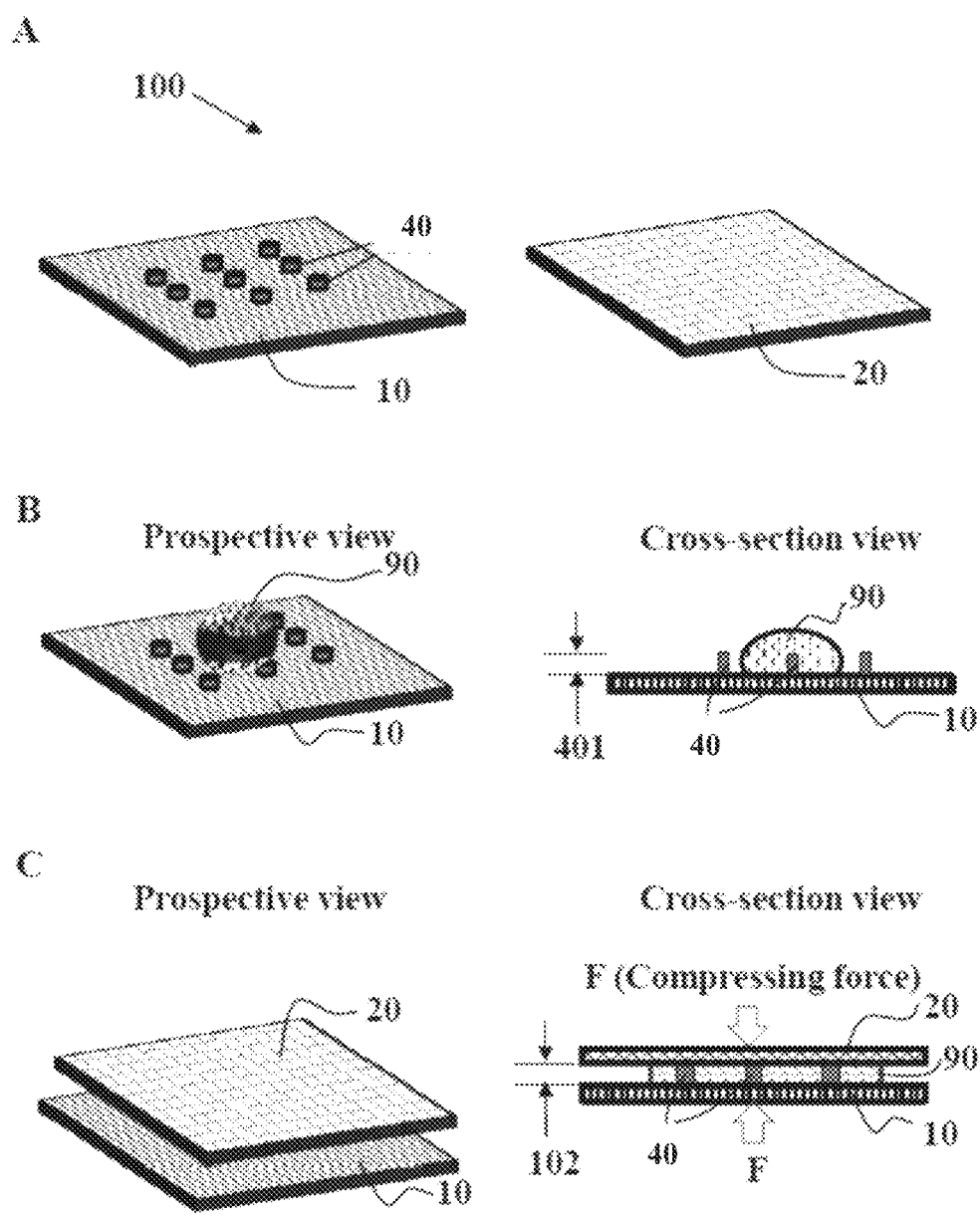
FIG. 1 shows an embodiment of a QMAX (Q: quantification; M: magnifying; A: adding reagents; X: acceleration; also known as compressed regulated open flow (CROF)) device, which comprises a first plate and a second plate. Panel (A) shows the perspective view of the plates in an open configuration when the plates are separated apart; panel (B) shows the perspective view and a sectional view of depositing a sample on the first plate at the open configuration; panel (C) the perspective view and a sectional view of the QMAX device in a closed configuration.

FIG. 1 shows an embodiment of a generic QMAX (Q: quantification; M: magnifying; A: adding reagents; X: acceleration; also known as compressed regulated open flow (CROF)) device. The generic QMAX device comprises a first plate 10 and a second plate 2. In particular, panel (A) shows the perspective view of a first plate 10 and a second plate 20 wherein the first plate has spacers. It should be noted, however, that the spacers can also be fixed on the second plate 20 (not shown) or on both first plate 10 and second plate 20 (not shown). Panel (B) shows the perspective view and a sectional view of depositing a sample 90 on the first plate 10 at an open configuration. It should be noted, however, that the sample 90 also can also be deposited on the second plate 20 (not shown), or on both the first plate 10 and the second plate 20 (not shown). Panel (C) illustrates (i) using the first plate 10 and second plate 20 to spread the sample 90 (the sample flow between the inner surfaces of the plates) and reduce the sample thickness, and (ii) using the spacers and the plate to regulate the sample thickness at the closed configuration of the QMAX device. The inner surfaces of each plate have one or a plurality of binding sites and or storage sites (not shown).

In some embodiments, the spacers 40 have a predetermined uniform height and a predetermined uniform inter-spacer distance. In the closed configuration, as shown in panel (C) of FIG. 1, the spacing between the plates and the thus the thickness of the sample 90 is regulated by the spacers 40. In some embodiments, the uniform thickness of the sample 90 is substantially similar to the uniform height of the spacers 40. It should be noted that although FIG. 1 shows the spacers 40 to be fixed on one of the plates, in some embodiments the spacers are not fixed. For example, in certain embodiments the spacers are mixed with the sample so that when the sample is compressed into a thin layer, the spacers, which is rigid beads or particles that have a uniform size, regulate the thickness of the sample layer.

QMAX Assay

In biological and chemical assaying (i.e. testing), a device and/or a method that simplifies assaying operation or accelerates assaying speed is often of great value.

In the QMAX (Q: quantification; M: magnifying; A: adding reagents; X: acceleration; also known as compressed regulated open flow (CROF)) assay platform, a QMAX card uses two plates to manipulate the shape of a sample into a thin layer (e.g. by compressing) (as illustrated in FIG. 1). In certain embodiments, the plate manipulation needs to change the relative position (termed: plate configuration) of the two plates several times by human hands or other external forces. There is a need to design the QMAX card to make the hand operation easy and fast.

In QMAX assays, one of the plate configurations is an open configuration, wherein the two plates are completely or partially separated (the spacing between the plates is not controlled by spacers) and a sample can be deposited. Another configuration is a closed configuration, wherein at least part of the sample deposited in the open configuration is compressed by the two plates into a layer of highly uniform thickness, the uniform thickness of the layer is confined by the inner surfaces of the plates and is regulated by the plates and the spacers.

In a QMAX assay operation, an operator needs to first make the two plates to be in an open configuration ready for sample deposition, then deposit a sample on one or both of the plates, and finally close the plates into a close position.

In certain embodiments, the two plates of a QMAX card are initially on top of each other and need to be separated to get into an open configuration for sample deposition. When one of the plate is a thin plastic film (175 um thick PMA), such separation can be difficult to perform by hand. The present invention intends to provide the devices and methods that make the operation of certain assays, such as the QMAX card assay, easy and fast.

In some embodiments, the QMAX device comprises a hinge that connects the two or more plates, so that the plates can open and close in a similar fashion as a book.

In certain embodiments, the hinge is configured so that the hinge can self-maintain the angle between the plates after adjustment.

In certain embodiments, the hinge is configured so that the material of the hinge, which maintain the QMAX card in the closed configuration, such that the entire QMAX card can be slide in and slide out a card slot without causing accidental separation of the two plates.

Another aspect of the present invention is to provide opening mechanisms such as but not limited to notches on plate edges or strips attached to the plates, making is easier for a user to manipulate the positioning of the plates, such as but not limited to separating the plates of by hand.

Another aspect of the present invention is to provide a hinge that can control the rotation of more than two plates.

The term "compressed open flow (COF)" refers to a method that changes the shape of a flowable sample deposited on a plate by (i) placing other plate on top of at least a part of the sample and (ii) then compressing the sample between the two plates by pushing the two plates towards each other; wherein the compression reduces a thickness of at least a part of the sample and makes the sample flow into open spaces between the plates. The term "compressed regulated open flow" or "CROF" (or "self-calibrated compressed open flow" or "SCOF" or "SCCOF") (also known as QMAX) refers to a particular type of COF, wherein the final thickness of a part or entire sample after the compression is "regulated" by spacers, wherein the spacers are placed between the two plates. Here the CROF device is used interchangeably with the QMAX device.

The term "spacers" or "stoppers" refers to, unless stated otherwise, the mechanical objects that set, when being placed between two plates, a limit on the minimum spacing between the two plates that can be reached when compressing the two plates together. Namely, in the compressing, the spacers will stop the relative movement of the two plates to prevent the plate spacing becoming less than a preset (i.e. predetermined) value.

The term "a spacer has a predetermined height" and "spacers have a predetermined inter-spacer distance" means, respectively, that the value of the spacer height and the inter spacer distance is known prior to a QMAX process. It is not predetermined, if the value of the spacer height and the inter-spacer distance is not known prior to a QMAX process. For example, in the case that beads are sprayed on a plate as spacers, where beads are landed at random locations of the plate, the inter-spacer distance is not predetermined. Another example of not predetermined inter spacer distance is that the spacers moves during a QMAX processes.

The term "a spacer is fixed on its respective plate" in a QMAX process means that the spacer is attached to a location of a plate and the attachment to that location is maintained during a QMAX (i.e. the location of the spacer on respective plate does not change) process. An example of "a spacer is fixed with its respective plate" is that a spacer is monolithically made of one piece of material of the plate, and the location of the spacer relative to the plate surface does not change during the QMAX process. An example of "a spacer is not fixed with its respective plate" is that a spacer is glued to a plate by an adhesive, but during a use of the plate, during the QMAX process, the adhesive cannot hold the spacer at its original location on the plate surface and the spacer moves away from its original location on the plate surface.

The term "open configuration" of the two plates in a QMAX process means a configuration in which the two plates are either partially or completely separated apart and the spacing between the plates is not regulated by the spacers The term "closed configuration" of the two plates in a QMAX process means a configuration in which the plates are facing each other, the spacers and a relevant volume of the sample are between the plates, the relevant spacing between the plates, and thus the thickness of the relevant volume of the sample, is regulated by the plates and the spacers, wherein the relevant volume is at least a portion of an entire volume of the sample.

The term "a sample thickness is regulated by the plate and the spacers" in a QMAX process means that for a give condition of the plates, the sample, the spacer, and the plate compressing method, the thickness of at least a port of the sample at the closed configuration of the plates can be predetermined from the properties of the spacers and the plate.

The term "inner surface" or "sample surface" of a plate in a QMAX device refers to the surface of the plate that touches the sample, while the other surface (that does not touch the sample) of the plate is termed "outer surface".

The term "height" or "thickness" of an object in a QMAX process refers to, unless specifically stated, the dimension of the object that is in the direction normal to a surface of the plate. For example, spacer height is the dimension of the spacer in the direction normal to a surface of the plate, and the spacer height and the spacer thickness means the same thing.

The term "area" of an object in a QMAX process refers to, unless specifically stated, the area of the object that is parallel to a surface of the plate. For example, spacer area is the area of the spacer that is parallel to a surface of the plate.

The term of QMAX device refers the device that perform a QMAX (e.g. CROF) process on a sample, and have or not have a hinge that connect the two plates.

The term "QMAX device with a hinge and "QMAX card" are interchangeable.

The term "angle self-maintain", "angle self-maintaining", or "rotation angle self-maintaining" refers to the property of the hinge, which substantially maintains an angle between the two plates, after an external force that moves the plates from an initial angle into the angle is removed from the plates.

QMAX Device and Assay for Cell Counting

The QMAX device can be used to analyze fluid samples, such as but not limited to biological fluid samples. In some embodiments, the QMAX device is used to analyze a blood sample. For example, in certain embodiments, the QMAX device is used to measure the amount of certain analytes, e.g. counting of red blood cells (RBC), white blood cells (WBC), and/or subtypes of certain blood cells. In certain embodiments, the QMAX device can be used for the counting of WBC. In certain embodiments, staining reagents can be used to label the cells and structures, such as but not limited to RBC, WBC (including WBC subtypes), and platelets.

As shown in FIG. 1, various parameters of the QMAX device can vary based on specific tests. For example, in some embodiment, the spacer height is less than 0.2 um, 0.5 um, 0.8 um, 1 um, 1.2 um, 1.5 um, 1.8 um, 2 um, 3 um, 4 um, 5 um, 6 um, 7 um, 8 um, 9 um, 10 um, 11 um, 12 um, 13 um, 14 um, 15 um, 16 um, 17 um, 18 um, 19 um, 20 um, 25 um, 30 um, 35 um, 40 um, 45 um, 50 um, 60 um, 70 um, 75 um, 80 um, 90 um, 100 um, 125 um, 150 um, 175 um, 200 um, 250 um, 300 um, 350 um, 400 um, 450 um, 500 um, 600 um, 700 um, 800 um, 900 um, 1 mm, 2 mm, 3 mm, 4 mm, 5 mm, 10 mm, or in a range between any of the two values. In the closed configuration, the uniform thickness of the sample layer is substantially the same as the gap between the QMAX plates, which is substantially the same as the spacer height. Therefore, the descriptions to the spacer height also apply to the thickness of the sample layer and the QMAX gap, and vice versa.

In some embodiments of the QMAX assay, the sample is deposited to one or both of the plates in the open configuration; then the plates are pressed into a closed configuration so that at least part of the sample compressed into a layer of highly uniform thickness, which is stagnant to the plates and confined by the inner surfaces of the plates. In some embodiments, an analyte in the sample is measured. In certain embodiments, the analyte is a type of cells that can be counted. For example, in certain embodiments the sample is a blood sample and the analyte is red blood cells; in certain embodiments the sample is a blood sample and the analyte is white blood cells; in certain embodiments the sample is a blood sample and the analyte is white blood cell sub-types (including neutrophils, eosinophils, basophils, lymphocytes, and monocytes).

In some embodiments, when the QMAX device is in the closed configuration, a camera can be used to capture images of the sample layer. In certain embodiments, the camera can have a field of view (FoV), which is defined as the area of sample of which the image can be captured by the camera. In certain embodiments, the camera is part of a device, such as but not limited to a mobile device. In certain embodiments, the mobile device is a smart phone, a tablet computer, or a laptop computer. In some embodiments, the mobile device is a mobile communication device such as a smart phone. In certain embodiments, the camera has one lens; in certain embodiments, the camera has two lenses that are aligned parallel to each other.

In some embodiments, different spacer height (hence different sample thickness and QMAX gap) can affect the accuracy of the counting of certain cells, such as but not limited to white blood cells and sub-types of white blood cells. For example, for counting white blood cells (WBC), spacer height and FoV can affect the accuracy and consistency of the counting results. With an acceptable level of consistency, the direct counting results can be adjusted to reflect the real number of cells, providing basis for diagnostics and health guidance. In certain embodiments, one factor that needs to be considered is the consistency of "miss count" rate, which is the deviation of the results with a method being tested from the real number, which is usually established with a well-defined and well-accepted method. It should also be noted that the method herein disclosed can be applied to not only WBC counting, but also other assays.

The device and method of the current invention can be used to (1) count the white blood cells, (b) count the white blood cells sub-types (including neutrophils, eosinophils, basophils, lymphocytes, and monocytes), and (3) differentiate white blood cells, wherein the device further comprises spacers that regulate the spacing between the sample contact areas when the plates are in a closed configuration.

In some embodiments, the average thickness of the layer of uniform thickness is in the range of 5.0 um to 8.5 um.

In some embodiments, the average thickness of the layer of uniform thickness is in the range of 7.5 um to 10.5 um.

In some embodiments, the average thickness of the layer of uniform thickness is in the range of 9.5 um to 12.5 um.

In some embodiments, the average thickness of the layer of uniform thickness is in the range of 9.5 um to 12.5 um.

In some embodiments, the average thickness of the layer of uniform thickness is in the range of 11.5 um to 13.5 um.

In some embodiments, the average thickness of the layer of uniform thickness is in the range of 12.5 um to 14.5 um.

In some embodiments, the average thickness of the layer of uniform thickness is in the range of 13.5 um to 16 um.

In some embodiments, the spacer height is in the range of 5.0 um to 8.5 um.

In some embodiments, the spacer height is in the range of 7.5 um to 10.5 um.

In some embodiments, the spacer height is in the range of 9.5 um to 12.5 um.

In some embodiments, the spacer height is in the range of 9.5 um to 12.5 um.

In some embodiments, the spacer height is in the range of 11.5 um to 13.5 um.

In some embodiments, the spacer height is in the range of 12.5 um to 14.5 um.

In some embodiments, the spacer height is in the range of 13.5 um to 16 um.

In some embodiments, the field of view for counting and differentiating WBCs is 0.1 mm$^2$, 10 mm$^2$, 50 mm$^2$, 100 mm$^2$ or a range between any two of the values.

In some embodiments, when the gap size of the QMAX device is about 10 um, the FoV is larger than 36 mm$^2$, thereby the WBC counting and differentiation accuracy is less than 5%.

In some embodiments, when the gap size of device is 10 um, the FoV is larger than 16 mm$^2$, thereby the WBC counting and differentiation accuracy is less than 10%.

In some embodiments, when the gap size of device is 10 um, the FoV is larger than 2 mm$^2$, thereby the WBC counting and differentiation accuracy is less than 20%.

In some embodiments, the field of view is in the range of 0.1 mm$^2$ to 10 mm$^2$, the preferred gap size of device is in the range of 10 um to 30 um, 30 um to 50 um, thereby the counting and differentiation accuracy is less than 10%.

In some embodiments, the field of view is in the range of 0.1 mm$^2$ to 10 mm$^2$, the preferred gap size of device is in the range of 10 um to 30 um, thereby the counting and differentiation accuracy is less than 20%.

In some embodiments, the field of view is in the range of 10 mm$^2$ to 50 mm$^2$, the preferred gap size of device is in the range of 5 um to 10 um, 10 um to 30 um, thereby the counting and differentiation accuracy is less than 10%.

In some embodiments, the field of view is in the range of 10 mm$^2$ to 50 mm$^2$, the preferred gap size of device is in the range of 2 um to 5 um, 5 um to 10 um, 10 um to 30 um, thereby the counting and differentiation accuracy is less than 20%.

In some embodiments, the field of view is in the range of 50 mm$^2$ to 100 mm$^2$, preferred gap size of device is in the range of 2 um to 5 um, 5 um to 10 um, 10 um to 30 um, 30 um to 50 um thereby the counting and differentiation accuracy is less than 10%.

In some embodiments, the spacer has a height of preferred range of 2 um to 5 um, thereby the WBCs missing counting is less than 15%.

In some embodiments, the spacer has a height of preferred range of 2 um to 5 um, 5 um to 10 um, thereby the WBCs missing counting is less than 30%.

In some embodiments, the spacer has a height of preferred range of 2 um to 5 um, 5 um to 10 um, 10 um to 30 um thereby the WBCs missing counting is less than 60%.

In some embodiments, the sample to camera lens distance is in the range of 2 mm to 5 mm.

In some embodiments, the sample to camera lens distance is in the range of 4 mm to 7 mm.

In some embodiments, the sample to camera lens distance is in the range of 6 mm to 9 mm.

In some embodiments, the sample to camera lens distance is in the range of 8 mm to 11 mm.

In some embodiments, the sample to camera lens distance is in the range of 10 mm to 13 mm.

In some embodiments, the sample to camera lens distance is in the range of 12 mm to 15 mm.

Examples of QMAX Device for Counting White Blood Cells

Figure 2:
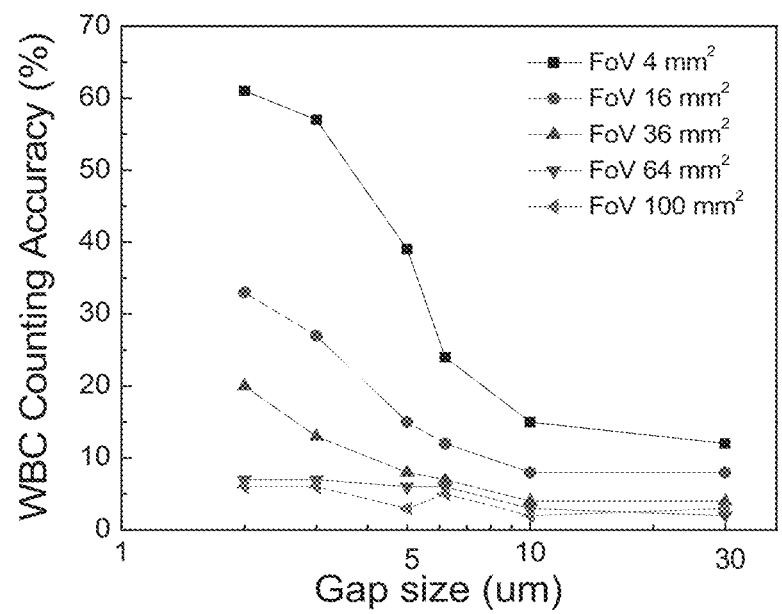
FIG. 2 illustrates white blood cell (WBC) counting accuracy vs. field of view (FoV) vs. QMAX gap (thickness of sample layer). Panel (A) shows plots of WBC counting accuracy vs. QMAX gap size with effective FoV of 4 mm$^2$, 16 mm$^2$, 36 mm$^2$, 64 mm$^2$, and 100 mm$^2$; panel (B) shows plots of WBC counting accuracy FoV with QMAX gap size of 2 um, 3 um, 5 um, 6.2 um, 10 um and 30 um.
Figure 2:
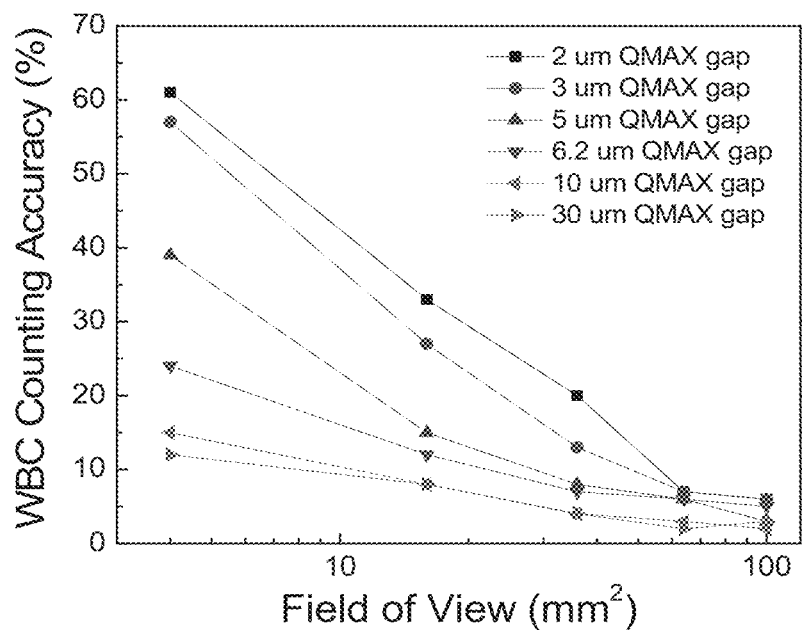

FIG. 2 illustrates white blood cell (WBC) counting accuracy vs. field of view (FoV) vs. QMAX gap (thickness of sample layer). Undiluted blood was deposited on one or both of the plates of the QMAX device in the open configuration; the plates were pressed into a closed configuration so that at least part of the sample was compressed into a layer of uniform thickness; a camera in a smart phone was used to capture images of the compressed sample; the number of WBC was counted by analyzing the images.

Panel (A) of FIG. 2 shows plots of WBC counting accuracy vs. QMAX gap size with effective FoV of 4 mm$^2$, 16 mm$^2$, 36 mm$^2$, 64 mm$^2$, and 100 mm$^2$; panel (B) shows plots of WBC counting accuracy FoV with QMAX gap size of 2 um, 3 um, 5 um, 6.2 um, 10 um and 30 um. The results are also summarized in Table 1.

TABLE 1

WBC counting accuracy vs. Field of View vs. QMAX gap

| Field of View (mm$^2$) | QMAX gap size (um) | | | | | |
|---|---|---|---|---|---|---|
| | 2 | 3 | 5 | 6.2 | 10 | 30 |
| 4 | 61% | 57% | 39% | 24% | 15% | 12% |
| 16 | 33% | 27% | 15% | 12% | 8% | 8% |
| 36 | 20% | 13% | 8% | 7% | 4% | 4% |
| 64 | 7% | 7% | 6% | 6% | 3% | 2% |
| 100 | 6% | 6% | 3% | 5% | 2% | 3% |

In this set of experiments, the first plate of the QMAX device is 1 mm thick PMMA with printed acridine orange dye, and the second plate is X-Plate with spacers having 30×40 um pillar size, 80 um inter spacing distance, made on 175 um thick PMMA. 1 uL fresh blood without any anti-coagulant was used in the test and deposited on the first plate. Counting accuracy is defined as the counting number's standard deviation for all the fields on card with a specific FoV. This counting accuracy represents the case when a field with FoV in the sample layer is randomly picked for measure, how accurate it represents the average number of all the fields. Generally, WBC counting is more accurate with larger field of view and larger QMAX gap. In essence, counting accuracy here reflects the consistency of the method with specific gap size and field of view.

Table 2 shows the relationship between WBC miss counting and correction factor vs. QMAX gap. Herein, miss counting rate is defined as the percentage difference between the back-calculated WBC concentration (from counting number, counting area, filling factor, gap size) and sample's real WBC concentrations (measured by calibrated commercial hematology machine).

Correction factor=1/(1−Missing Counting Rate).

TABLE 2

WBC miss counting & correction factor vs. QMAX gap

| QMAX gap size (um) | WBC miss counting | WBC correction factor |
|---|---|---|
| 2 | 0% | 1 |
| 3 | 0% | 1 |
| 5 | 10% | 1.1 |
| 10 | 25% | 1.3 |
| 30 | 50% | 2.0 |

As shown in Table 2, the miss counting rate increases with the gap size (thus spacer height and sample thickness). Furthermore, additional experiments show that differentiated WBC (Granulocytes, Lymphocyte, Monocyte) counting has similar miss counting rate with WBC total counting. In addition, WBC miss counting rate is not influenced by field of view.

Figure 3:
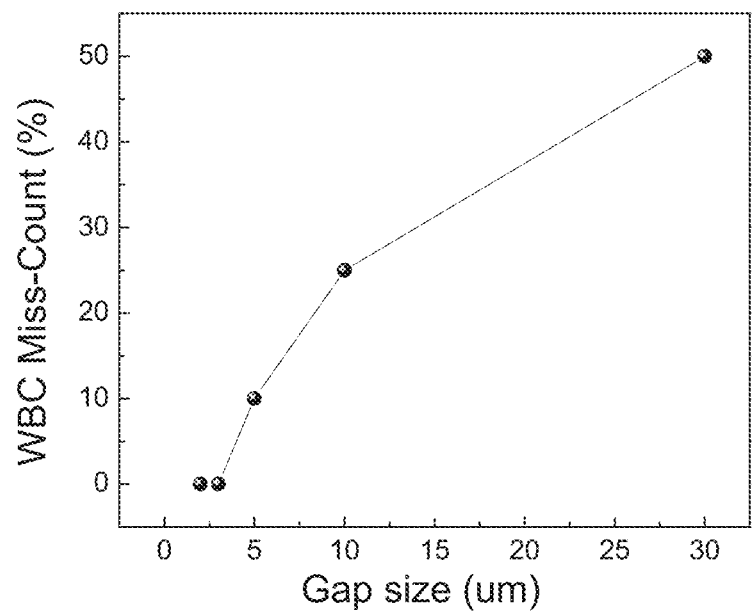
FIG. 3. Panel (A) illustrates plots of WBC miss count percentage vs. QMAX gap size (thickness of sample layer) of 2 um, 5 um, 10 um and 30 um. Panel (B) illustrates plots of QMAX transmittance at 500 nm wavelength (which is close to fluorescence of WBCs) vs. QMAX gap size.
Figure 3:
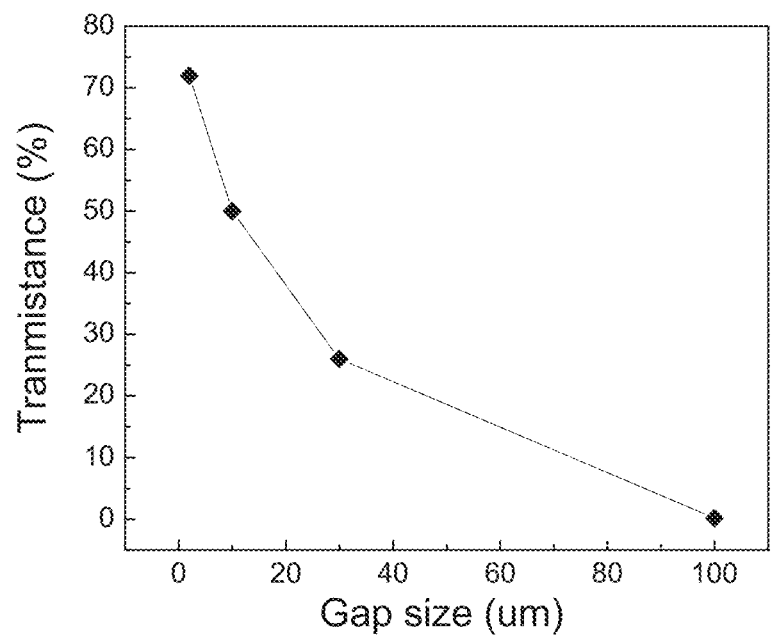

Panel (A) of FIG. 3 illustrates plots of WBC miss count percentage vs. QMAX gap size (thickness of sample layer; spacer height) of 2 um, 5 um, 10 um and 30 um. Panel (B) of FIG. 3 illustrates plots of QMAX transmittance at 500 nm wavelength (which is close to fluorescence of WBCs) vs. QMAX gap size.

As shown in FIG. 3, panels (A) and (B), more WBCs are miss counted with larger gap size (thicker blood film). One of the reason is fluorescence from WBC is dimmed and blocked by the RBCs with thicker blood film as shown in the (b) transmittance vs. gap size. Therefore, it means larger QMAX gap, more WBC are miss-counted. However, as shown in FIG. 2, panels (A) and (B), the counting accuracy, which reflects the consistency of the counting at certain gap sizes and field of view, is higher with a larger gap size and a larger field of view, respectively. Therefore, in some embodiments, certain gap sizes (thus spacer heights) and/or field of view size can be chosen to obtain an acceptable level of consistency, and/or prevent high level of miss count.

With the correction factor, which is based on the miss counting rate, the counting result can be adjusted to provide a more accurate and consistent number for medical and health purposes. In some embodiments, the final number equals the counting results multiplies the correction factor. In certain embodiments, the correction factor can be obtained/calculated from Table 2 and/or FIG. 3.

Figure 4:
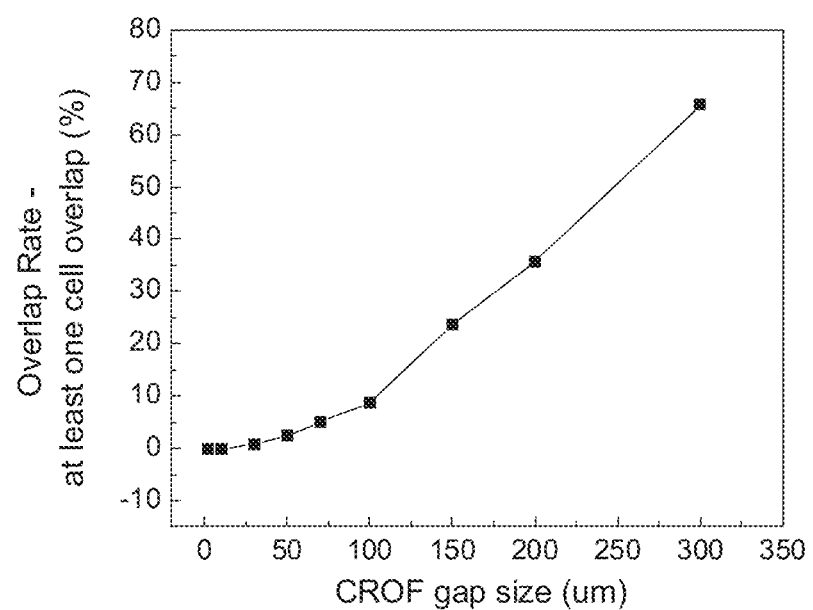
FIG. 4 shows the theoretical calculation of self-overlap rate of WBC cell vs. QMAX gap.

FIG. 4 shows the calculation of self-overlap rate of WBC cell vs. QMAX gap. The results are also shown in Table 3. In general, more WBCs are overlapped when the gap size is larger, especially larger than 30 um.

TABLE 3

QMAX gap size vs. WBC distance vs. Overlap rate

| CROF gap (um) | Cell 2D Distance (um) | Overlap Rate |
|---|---|---|
| 2 | 320 | 0% |
| 10 | 140 | 0% |
| 30 | 80 | 1% |
| 50 | 60 | 2% |
| 70 | 50 | 5% |

TABLE 3-continued

QMAX gap size vs. WBC distance vs. Overlap rate

| CROF gap (um) | Cell 2D Distance (um) | Overlap Rate |
|---|---|---|
| 100 | 45 | 9% |
| 300 | 25 | 66% |

Exemplary Embodiments with a Gap of 8 to 12 um

The experiments (see e.g. FIGS. 2-4) show that for the measurement of WBC in undiluted blood sample, with a given field of view provide by a camera (e.g. camera in a mobile phone), a spacer height of 5 to 15 um provides more accurate results than spacer height of 2 um to 3 um. In some embodiments, a QMAX device for WBC measurement has spacer height of 5 to 15 um. In certain embodiments, the QMAX device has a spacer height of 10 um, while a same of a similar sample thickness uniformity can be achieved. In some embodiments, such pillar heights have advantage for imaging and counting the white blood cells in an undiluted blood.

Exemplary Embodiments of Optical Adapter

In some embodiments, the QMAX device (e.g. in the form of a QMAX card) with sample can be inserted into an adaptor, which can be attached to a device that comprises a camera and/or an illumination source. In certain embodiments, the device is a mobile communication device, such as but not limited to a smart phone.

Figure 5:
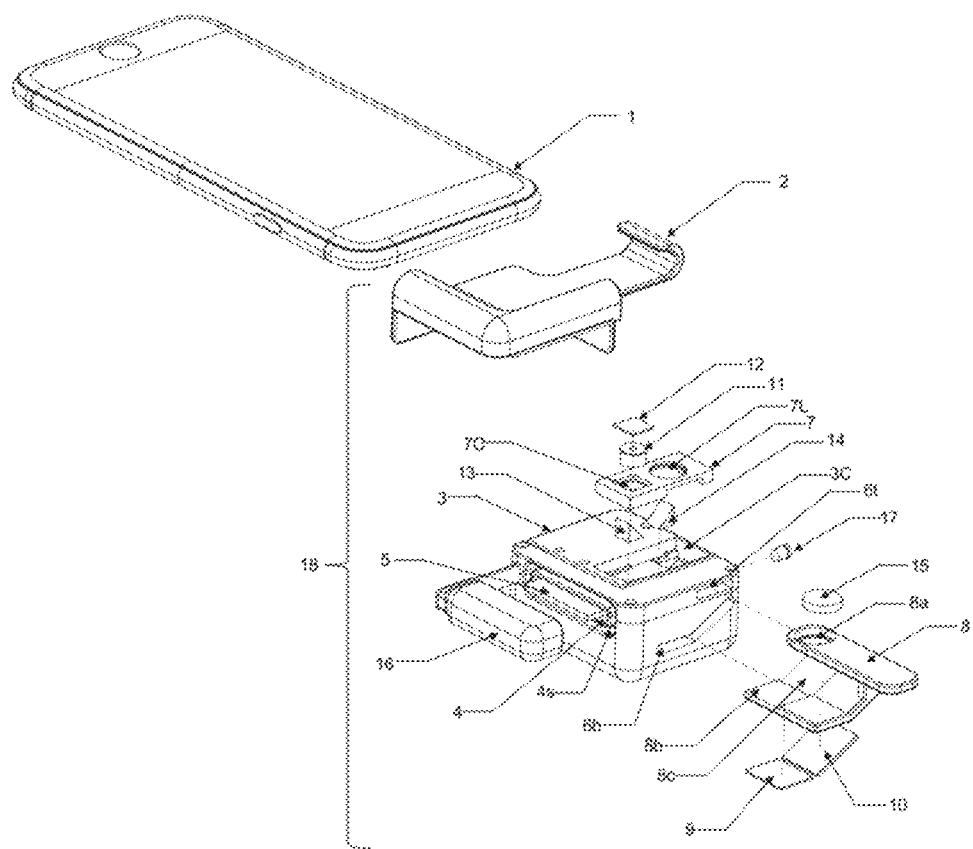
FIG. 5 shows a schematic exploded view of an optical adaptor device for attaching the QMAX device to a mobile communication device.

FIG. 5 shows a schematic exploded view of an optical adaptor device for attaching the QMAX device to a mobile communication device and for measurement of an analyte in the sample. Here the optical adaptor device 18 is in system 19, which comprises the mobile communication device (smart phone) 1.

adaptor 18 comprises a holder case 2 fitting over the upper part of smartphone 1; an optical box 3 attached to case 2 including a receptacle slot 4, an optics chamber 3C, track 6b and 6t allowing lever 8 to slide in, and a rubber door 16 inserted into trench 4s to cover receptacle slot 4. An optics insert 7 is fitted into the top of optics chamber 3C with an exit aperture 7L and an entrance aperture 7C in it aligning with light source 1L and camera 1C (referring to FIG. 6) in smartphone 1. A lens 11 is mounted in entrance aperture 7C in optics insert 7 and configured so that the sample in sample slide 5 inserted into receptacle slot 4 is located within the working distance of the camera 1C (referring to FIG. 6). Lens 11 serves to magnify the images of the sample captured by camera 1C (referring to FIG. 6). A long-pass optical filter 12 is mounted on top of lens 11 in entrance aperture 7C. A pair of right angle mirrors 13 and 14 are mounted on the bottom of optics chamber 3C and configured so that mirror 13 and mirror 14 are aligned with light source 1L and camera 1C (referring to FIG. 6) respectively. Mirror 13 and mirror 14 whose operation as bright-field illumination optics in device 18 is described below in FIG. 6.

Lever 8 comprises two level bars: the upper-level bar comprises a band-pass optical filter 15 mounted in slot 8a, and the lower-level bar comprises a light absorber 9 mounted on the horizontal plane 8b and a reflective mirror 10 mounted on the tilted plane 8c. The optical filter 15, light absorber 9 and mirror 10 whose operation as fluorescent illumination optics in device 18 is described in FIG. 6. The upper-level bar of lever 8 slides along track 6t in box 3 and lower-level bar 8b and 8c slides along track 6b in box 3. Lever 8 stops at two different positions in box 3 to switch between bright-field illumination optics and fluorescent illumination optics. Lever 8 is fully inserted into box 3 to switch device 18 to work with fluorescent illumination optics. Ball plunger 17 is mounted on the sidewall of track 6t to stop lever 8 at a pre-defined position when lever 8 being pulled outward from box 3 to switch device 18 to work with bright-field illumination optics.

Figure 6:
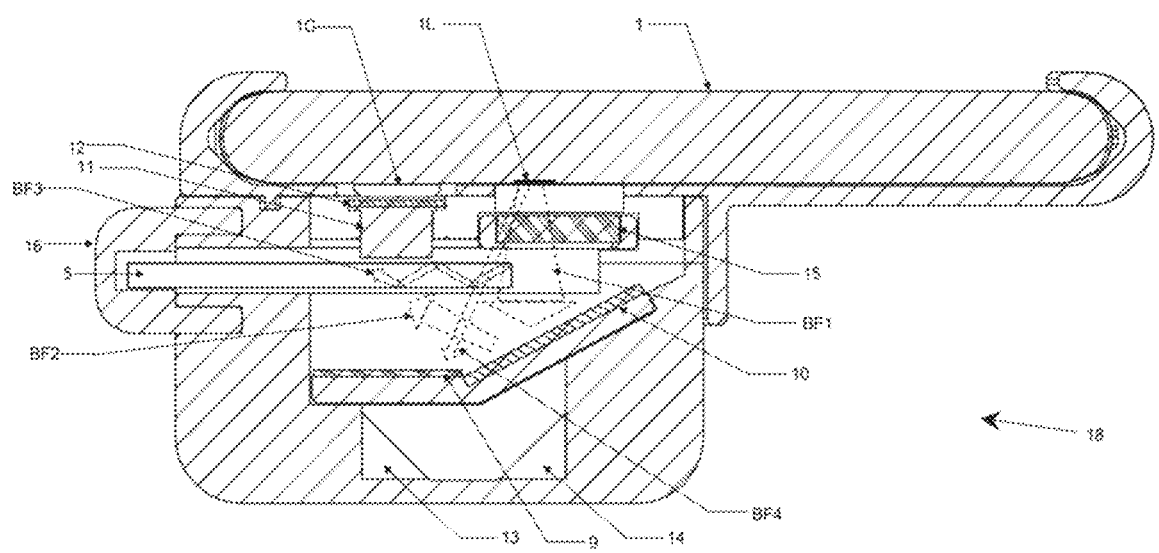
FIG. 6 shows a schematic sectional view with details of a system that can be used to test a sample in fluorescent illumination mode, and particularly of the optical adapter.

FIG. 6 shows a schematic sectional view with details of a system that can be used to test a sample in fluorescent illumination mode, and particularly of the optical adaptor. This Fig. illustrates the functionality of the elements that were described above with reference to FIG. 5. Lever 8 (shown in FIG. 5) is fully inserted into device 18 so that light absorber 9 and tilted mirror 10 are under the view of camera 1C and light source 1L, and block the light path between light source 1L and the pair of mirrors of 13 and 14. And band-pass optical filter 15 is right under the light source 1L. Light source 1L emits light beam BF1 away from smartphone 1. Optical filter 15 allows beam BF1 with specific wavelength range which matches the excitation wavelength of the fluorescent sample in sample slide 5 to go through. Part of beam BF1 illuminates on the edge of transparent sample slide 5 and couples to waveguide beam BF3 travelling in sample slide 5 and illuminates the sample area under the lens 11. Part of beam BF1 illuminates on mirror 10. Tilted mirror 10 deflects beam BF1 to beam BF2 and back-illuminates the sample area in sample slide 5 right under lens 11 in large oblique angle. The remaining part of beam BF1 with large divergence angle (i.e., beam BF4) illuminates on absorber 9 and get absorbed so that no reflected light of beam BF4 gets into the camera 1C in small incidence angle. The light coming from the sample area under the lens 11 goes through the lens 11 and is filtered by long-pass filter 12 so that only light in a specify wavelength range that is emitted by the fluorescent sample in sample slide 5 gets into camera 10 to form an image. Smartphone 1 captures and processes the image to get some property of the sample. Rubber door 16 is inserted into device 18 to cover sample slide 5 to prevent ambient light getting into device 18 to affect the test.

In some embodiments, the adapter as described in FIGS. 5 and 6 can be used to measure a blood sample, e.g. undiluted whole blood sample. In certain embodiments, the analyte can be WBC, which requires the lever 8 to be inserted for optimal reading. In some embodiments, the adapter comprises:
(a) an attachment member configured to attach the adapter to an apparatus that comprises a light source and a camera;
(b) a card slot configured to accommodate a sample card, which contains a liquid sample that is compressed into a layer of uniform thickness, wherein when the sample card inserted into the card slot, the sample is positioned under the view of the camera and the light source;
(c) an optical filter configured to filter light from the light source to form a first beam with a specific wavelength range, wherein a part of the first beam illuminates on the edge of the sample card and travels in the sample card to illuminate the sample;
(d) a mirror configured to deflect part of the first beam to form a second beam that back-illuminates the sample in an oblique angle;
(e) an absorber configured to absorb a remaining part of the first beam that has a divergence angle.

In some embodiments, the method to measure an analyte, such as but not limited to WBC, in a liquid sample, can comprises:

(a) obtaining the liquid sample;
(b) compressing at least part of the sample into a layer of uniform thickness with a sample card,
(c) inserting the sample card into an adaptor device, which is configured to be attached to an apparatus that comprises a light source and a camera;
(d) illuminating the sample with light from the light source, wherein
   i. the light is filtered by an optical filter of the adapter device to form a first beam with a specific wavelength range, part of the first beam illuminating on the edge of the sample card and travels in the sample card to illuminate the sample;
   ii. part of the first beam is deflected by a mirror of the adapter device to form a second beam that back-illuminates the sample in an oblique angle; and
   iii. a remaining part of the first beam that has a divergence angle is absorbed by an absorber of the adapter device.

In some embodiment, the method can further comprise:
(a) capturing images of the sample in the layer of uniform thickness with the camera;
(b) analyzing the images to enumerate the analyte in the images; and
(c) calculating the concentration of the analyte in the sample based on the uniform thickness, a field of view of the camera, analyte number, and a predetermined correction factor;
wherein the field of view is the extent of the field in which the camera captures the images;
wherein the correction factor is determined by a miscount ratio, which is dependent on the field of view, the uniform thickness, and properties of the analyte.

Exemplary Embodiments for WBC Measurement

For the device or method embodiments of the current invention, the device can further comprise, on one or both plates, multi reagent layers including anti-conglutination reagents, cell lysing reagents, cell staining reagents, release time control material, and any combinations thereof.

In some embodiments, each reagent layer coated on the plates has a thickness of 10 nm, 100 nm, 200 nm, 500 nm, 1 um or in a range between any two of the values.

In some embodiments, the anti-conglutination agent comprises ethylenediaminetetraacetic acid (EDTA), EDTA disodium, K2EDTA, or K3EDTA, or any combinations thereof.

In some embodiments, the cell stain agent comprises Wright's stain (Eosin, methylene blue), Giemsa stain (Eosin, methylene blue, and Azure B), May-Grünwald stain, Leishman's stain ("Polychromed" methylene blue (i.e. demethylated into various azures) and eosin), Erythrosine B stain (Erythrosin B), and other fluorescence stain including but not limit to Acridine orange dye, 3,3-dihexyloxacarbocyanine (DiOC6), Propidium Iodide (PI), Fluorescein Isothiocyanate (FITC) and Basic Orange 21 (BO21) dye, Ethidium Bromide, Brilliant Sulfaflavine and a Stilbene Disulfonic Acid derivative, Erythrosine B or trypan blue, Hoechst 33342, Trihydrochloride, Trihydrate, or DAPI (4',6-Diamidino-2-Phenylindole, Dihydrochloride), or any combinations thereof.

In some embodiments, the cell lysing agent comprises ammonium chloride, sodium bicarbonate, ethylenediaminetetraacetic acid (EDTA), acetic acid, citric acid, or other acid and base, or any combinations thereof.

In some embodiments, the release time control material comprises albumin, carbomers, carboxymethyl cellulose, carrageenan, chitosan, dextrin, polyethylene glycol, polyvinylpyrrolidone, or polyvinyl alcohol, or any combinations thereof.

In some embodiments of the method embodiments of the current invention, the RBCs, platelets, or both are lysed in the sample before the detection and/or measurement of WBCs.

In some embodiments of the method embodiments of the current invention, the WBCs, platelets, or both are lysed in sample before the detection of RBCs.

In some embodiments of the method embodiments of the current invention, the RBCs, WBCs, or both are lysed in sample before the detection of PLTs.

Group of Other Examples of Present Invention

Further examples of inventive subject matter according to the present disclosure are described in the following enumerated paragraphs.

Correction Factor and Field of View

A1. A method for analyzing an analyte in a liquid sample, comprising:
 (a) obtaining the liquid sample;
 (b) compressing at least part of the sample into a layer of uniform thickness,
 (c) capturing images of the sample in the layer of uniform thickness with a camera, wherein the images show the analyte; and
 (d) analyzing the images to enumerate the analyte in the images,
 (e) calculating the concentration of the analyte in the sample based on the uniform thickness, a field of view of the camera, the analyte enumeration, and a predetermined correction factor;
 wherein the field of view is the extent of the field in which the camera captures the images;
 wherein the correction factor is determined by a miscount ratio, which is dependent on the field of view, the uniform thickness, and properties of the analyte.

Illumination for WBC

B1. An adapter device for analyzing an analyte in a liquid sample, comprising:
 (a) an attachment member configured to attach the adapter to an apparatus that comprises a light source and a camera;
 (b) a card slot configured to accommodate a sample card, which contains a liquid sample that is compressed into a layer of uniform thickness, wherein when the sample card inserted into the card slot, the sample is positioned under the view of the camera and the light source;
 (c) an optical filter configured to filter light from the light source to form a first beam with a specific wavelength range, wherein a part of the first beam illuminates on the edge of the sample card and travels in the sample card to illuminate the sample;
 (d) a mirror configured to deflect part of the first beam to form a second beam that back-illuminates the sample in an oblique angle;
 (e) an absorber configured to absorb a remaining part of the first beam that has a divergence angle.

B2. A method for analyzing an analyte in a liquid sample, comprising:
 (a) obtaining the liquid sample;
 (b) compressing at least part of the sample into a layer of uniform thickness with a sample card,
 (c) inserting the sample card into an adaptor device, which is configured to be attached to an apparatus that comprises a light source and a camera;
 (d) illuminating the sample with light from the light source, wherein
  i. the light is filtered by an optical filter of the adapter device to form a first beam with a specific wavelength range, part of the first beam illuminating on the edge of the sample card and travels in the sample card to illuminate the sample;
  ii. part of the first beam is deflected by a mirror of the adapter device to form a second beam that back-illuminates the sample in an oblique angle; and
  iii. a remaining part of the first beam that has a divergence angle is absorbed by an absorber of the adapter device.

B3. The method of embodiment B2, further comprising:
 (a) capturing images of the sample in the layer of uniform thickness with the camera;
 (b) analyzing the images to enumerate the analyte in the images; and
 (c) calculating the concentration of the analyte in the sample based on the uniform thickness, a field of view of the camera, analyte number, and a predetermined correction factor;
 wherein the field of view is the extent of the field in which the camera captures the images;
 wherein the correction factor is determined by a miscount ratio, which is dependent on the field of view, the uniform thickness, and properties of the analyte.

Additional Features:

C1. The device or method of any prior embodiments, wherein the liquid sample is a blood sample.

C2. The device or method of any prior embodiments, wherein the analyte is white blood cells (WBC).

C3. The device or method of any prior embodiments, wherein the analyte is a WBC subtype.

C4. The device or method of any prior embodiments, wherein the analyte is neutrophils, eosinophils, basophils, lymphocytes, or monocytes.

C5. The device or method of any prior embodiments, wherein the analyte is marked with fluorescence.

C6. The device or method of any prior embodiments, wherein the uniform thickness is in the range of 5 to 30 um.

C7. The device or method of any prior embodiments, wherein the uniform thickness is in the range of 8 to 12 um.

C8. The device or method of any prior embodiments, wherein the uniform thickness is around 10 um.

C9. The device or method of any prior embodiments, wherein the field of view (FOV) is equal to or larger than 4 $mm^2$.

C10. The device or method of any prior embodiments, wherein the field of view (FOV) is equal to or larger than 16 $mm^2$.

C11. The device or method of any prior embodiments, wherein the field of view (FOV) is equal to or larger than 36 $mm^2$.

C12. The device or method of any prior embodiments, wherein the field of view (FOV) is equal to or larger than 64 $mm^2$.

C13. The device or method of any prior embodiments, wherein the field of view (FOV) is equal to or larger than 100 $mm^2$.

C14. The device or method of any prior embodiments, wherein the correction factor is 1 when the sample thickness is 2 mm, the correction factor is 1 when the sample thickness is 3 mm, the correction factor is 1.1 when the sample thickness is 5 mm, the correction factor is 1.3 when the sample thickness is 10 mm, and the correction factor is 2.0 when the sample thickness is 30 mm.

C15. The device or method of any prior embodiments, wherein the analyte is marked with fluorescence and the wavelength range of the first beam matches the excitation wavelength of the fluorescence marking the analyte.

C15. The device or method of any prior embodiments, wherein the adaptor device further comprises a housing member.

C16. The device or method of any prior embodiments, wherein the adaptor device further comprises a lever, which can be inserted into or extracted from the housing member.

C17. The device or method of any prior embodiments, wherein the mirror and the absorber are mounted on the lever.

C18. The device or method of any prior embodiments, wherein adaptor device comprises a card slot that has a secured opening that allows the insertion of the sample card and prevents ambient light from entering the card slot.

WBC Analysis Device

AA1. A device for analyzing white blood cells in a blood sample, comprising:
a first plate, a second plate, and spacers, wherein:
i. the plates are movable relative to each other into different configurations;
ii. one or both plates are flexible;
iii. each of the plates comprises an inner surface that has a sample contact area for contacting a blood sample;
iv. one or both of the plates comprise the spacers that are permanently fixed on the sample contact area of a respective plate;
v. the spacers have:
(a) a predetermined substantially uniform height that has a value selected in the range of 2 um to 30 um,
(b) a shape of pillar with substantially uniform cross-section and a flat top surface;
(c) a ratio of the width to the height equal to or larger than one;
(d) a predetermined, fixed, non-random, inter-spacer distance that is in the range of 10 um to 200 um (micron);
(e) a filling factor of equal to 1% or larger, wherein the filling factor is the ratio of the spacer contact area (on the plate) to the total plate area; and
(f) the filling factor multiplies the Young's modulus of the spacer is equal to 2 MPa or larger;
wherein one of the configurations is an open configuration, in which: the two plates are partially or completely separated apart, the spacing between the plates is not regulated by the spacers, and the sample is deposited on one or both of the plates;
wherein another of the configurations is a closed configuration which is configured after the sample is deposited in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

AA2. A device for analyzing white blood cells in a blood sample, comprising:
a first plate, a second plate, spacers, and adaptor wherein:
i. the plates are movable relative to each other into different configurations;
ii. one or both plates are flexible;
iii. each of the plates comprises an inner surface that has a sample contact area for contacting a fluidic sample;
iv. one or both of the plates comprise the spacers that are permanently fixed on the sample contact area of a respective plate;
v. the spacers have:
(a) a predetermined substantially uniform height that has a value selected in the range of 2 um to 30 um,
(b) a shape of pillar with substantially uniform cross-section and a flat top surface;
(c) a ratio of the width to the height equal or larger than one;
(d) a predetermined fixed, non-random, inter-spacer distance that is in the range of 10 um to 200 um;
(e) a filling factor of equal to 1% or larger, wherein the filling factor is the ratio of the spacer contact area (on the plate) to the total plate area; and
(f) the filling factor multiplies the Young's modulus of the spacer is equal to 2 MPa or larger;
vi. the adaptor comprises: (a) a housing, (b) an attachment member on the housing that allows the adaptor to be attached to a mobile phone with a camera, (c) a slot in the housing that allows (1) the plates in a closed configuration to slide into the slot and (2) when the plates are in the slot, at least a part of the sample area is less than 2 cm away from the outer surface of the camera, and (d) an optical system in the housing configured to have at least a part of the sample contact area be imaged by the camera;
wherein one of the configurations is an open configuration, in which: the two plates are partially or completely separated apart, the spacing between the plates is not regulated by the spacers, and the sample is deposited on one or both of the plates;
wherein another of the configurations is a closed configuration which is configured after the sample is deposited in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

AA3. A device for analyzing white blood cells in a blood sample, comprising:
a first plate, a second plate, spacers, and adaptor wherein:
i. the plates are movable relative to each other into different configurations;
ii. one or both plates are flexible;
iii. each of the plates comprises an inner surface that has a sample contact area for contacting a fluidic sample;
iv. one or both of the plates comprise the spacers that are permanently fixed on the sample contact area of a respective plate;
v. the spacers have:
(a) a predetermined substantially uniform height that has a value selected in the range of 10 um to 50 um,
(b) a shape of pillar with substantially uniform cross-section and a flat top surface;
(c) a ratio of the width to the height equal or larger than one;
(d) a predetermined fixed, non-random, inter-spacer distance that is in the range of 10 um to 200 um;
(e) a filling factor of equal to 3% or larger, wherein the filling factor is the ratio of the spacer contact area (on the plate) to the total plate area; and
(f) the filling factor multiplies the Young's modulus of the spacer is equal to 2 MPa or larger;
vi. one or both of the plates comprise the reagents that are coated on the sample contact area of a respective plate;

vii. the reagents have at least one of the following: (a) a component to stain the WBC; (b) a component to make the RBC distribution uniform; (c) a component to lyse the RBC;

viii. the adaptor comprises: (a) a housing, (b) an attachment member on the housing that allows the adaptor to be attached to a mobile phone with a camera, (c) a slot in the housing that allows (1) the plates in a closed configuration to slide into the slot and (2) when the plates are in the slot, at least a part of the sample area is less than 2 cm away from the outer surface of the camera, and (d) an optical system in the housing configured to have at least a part of the sample contact area be imaged by the camera;

wherein one of the configurations is an open configuration, in which: the two plates are partially or completely separated apart, the spacing between the plates is not regulated by the spacers, and the sample is deposited on one or both of the plates;

wherein another of the configurations is a closed configuration which is configured after the sample is deposited in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

AA4. A method for analyzing white blood cells in a blood sample, comprising:
(a) obtaining a blood sample;
(b) obtaining a device of AA1 or AA2 or AA3;
(c) depositing the blood sample on one or both of the plates when the plates are configured in the open configuration,
(d) after (c), forcing the two plates into a closed configuration; and
(e) capturing images of sample in the layer of uniform thickness while the plates are the closed configuration; and
(f) analyzing the images to determine the concentration of white blood cells in the sample.

AA5 A method for white blood cell and sub-type (including neutrophils, eosinophils, basophils, lymphocytes, and monocytes) counting using a single device, comprising:
(a) obtaining a blood sample;
(b) obtaining the device of any prior embodiments, wherein the spacer height is 5 um to 40 um,
(c) depositing the blood sample on one or both of the plates when the plates are configured in an open configuration;
(d) after (c), forcing the two plates into a closed configuration;
(e) capturing images of the sample in the layer of uniform thickness while the plates are the closed configuration; and
(f) analyzing the images to determine the respective number of white blood cells, neutrophils, lymphocytes, monocytes, eosinophils and basophils, through the counting of the cell number in the image and the analysis of the fluorescence color (means the emission wavelength range) and shape for each white blood cell.

BB1. The device or method of any prior embodiments, wherein the blood sample is undiluted.

BB2. The device or method of any prior embodiments, wherein the staining and shape of white blood cell provide fluorescence color, structure and dimension distinguish of white blood cell and its subtypes and white blood cell differentiation.

The device or method of any prior embodiments, wherein the fluorescence color (means the emission wavelength range) is used for WBC count and differentiate;

The device or method of any prior embodiments, wherein the dimension is used for WBC count and differentiate;

The device or method of any prior embodiments, wherein the structure of WBC is used for WBC count and differentiate;

The device or method of any prior embodiments, wherein both the color (means the emission wavelength range) and the structure of WBC is used for WBC count and differentiate;

The device or method of any prior embodiments, wherein color (means the emission wavelength range) of white blood cell is distinguished by the image's Red, Green, Blue channel.

The device or method of any prior embodiments, wherein color (means the emission wavelength range) of white blood cell is distinguished by the filters at different wavelength before camera.

The device or method of any prior embodiments, wherein color (means the emission wavelength range) of white blood cell is distinguished by the filters at different wavelength before light source.

The device or method of any prior embodiments, wherein the color (means the emission wavelength range) of white blood cell is from WBC staining from one chemical as acridine orange dye.

The device or method of any prior embodiments, wherein the color (means the emission wavelength range) of white blood cell is from WBC staining from different chemicals.

The device or method of any prior embodiments, wherein white blood cells are stained by propidium Iodide (PI), Fluorescein Isothiocyanate (FITC) and Basic Orange (BO21). PI is a red nucleic acid dye, which stains DNA and shows red fluorescence. FITC stains cytoplasmic proteins and shows green fluorescence. BO21 is green nucleic acid dye which stains DNA and shows green fluorescence. Combination of these three fluorescent dyes can distinguish different types of white blood cells such as lymphocyte, monocyte, neutrophil and eosinophil.

The device or method of any prior embodiments, wherein the shape of white blood cell is analyzed by machine learning.

The device or method of any prior embodiments, wherein the color (means the emission wavelength range) and shape of white blood cell is analyzed by machine learning.

BB3. The device or method of any prior embodiments, wherein the device further comprises, on one or both plates, multi reagent layers including anti-conglutination, cell lysing, cell staining, release time control material layers, or their combinations.

CC1. The device or method of any prior embodiments, wherein the pillar height is in the range of 5 to 15 um, CC2. The device or method of any prior embodiments, wherein the pillar height is in the range of 8 to 12 um, CC3. The device or method of any prior embodiments, wherein the pillar height is around 10 um.

CC3. The device or method of any prior embodiments, wherein the pillar height is around 30 um.

CC4. The device or method of any prior embodiments, wherein the device is configured to count the white blood cells.

CC5. The device or method of any prior embodiments, wherein the device is configured to count the white blood cells sub-types (including neutrophils, eosinophils, basophils, lymphocytes, and monocytes), CC6. The device or method of any prior embodiments, wherein spacer height is in the range of 7.5 um to 10.5 um.

CC7. The device or method of any prior embodiments, wherein spacer height is in the range of 9.5 um to 12.5 um.

CC8. The device or method of any prior embodiments, wherein spacer height is in the range of 11.5 um to 13.5 um.

CC9. The device or method of any prior embodiments, wherein spacer height is in the range of 12.5 um to 14.5 um.

CC10. The device or method of any prior embodiments, wherein spacer height is in the range of 13.5 um to 15 um.

CC10. The device or method of any prior embodiments, wherein spacer height is in the range of 15 um to 18 um.

CC10. The device or method of any prior embodiments, wherein spacer height is in the range of 18 um to 25 um.

CC10. The device or method of any prior embodiments, wherein spacer height is in the range of 25 um to 30 um.

CC10. The device or method of any prior embodiments, wherein spacer height is in the range of 30 um to 35 um.

CC10. The device or method of any prior embodiments, wherein spacer height is in the range of 35 um to 40 um.

CC10. The device or method of any prior embodiments, wherein spacer height is in the range of 40 um to 50 um.

CC11. The device or method of any prior embodiments, wherein a preferred field of view for counting and differentiating WBCs is 0.1 mm$^2$, 10 mm$^2$, 50 mm$^2$, 100 mm$^2$ or a range between any two of the values;

CC12. The device or method of any prior embodiments, wherein when the gap size of device is 10 um, the FoV is larger than 36 mm$^2$, thereby the WBC counting and differentiate accuracy is less than 5%.

CC13. The device or method of any prior embodiments, wherein when the gap size of device is 10 um, the FoV is larger than 16 mm$^2$, thereby the WBC counting and differentiate accuracy is less than 10%.

CC14. The device or method of any prior embodiments, wherein when the gap size of device is 10 um, the FoV is larger than 2 mm$^2$, thereby the WBC counting and differentiate accuracy is less than 20%.

CC15. The device or method of any prior embodiments, wherein a field of view is 0.1 mm$^2$ to 10 mm$^2$, preferred gap size of device is in the range of 10 um to 30 um, 30 um to 50 um, thereby the counting and differentiate accuracy is less than 10%.

CC16. The device or method of any prior embodiments, wherein field of view is 0.1 mm$^2$ to 10 mm$^2$, preferred gap size of device is in the range of 10 um to 30 um, thereby the counting and differentiate accuracy is less than 20%.

CC17. The device or method of any prior embodiments, wherein field of view is 10 mm$^2$ to 50 mm$^2$, preferred gap size of device is in the range of 5 um to 10 um, 10 um to 30 um, thereby the counting and differentiate accuracy is less than 10%.

CC18. The device or method of any prior embodiments, wherein field of view is 10 mm$^2$ to 50 mm$^2$, preferred gap size of device is in the range of 2 um to 5 um, 5 um to 10 um, 10 um to 30 um, thereby the counting and differentiate accuracy is less than 20%.

CC19. The device or method of any prior embodiments, wherein field of view is field of view of 50 mm$^2$ to 100 mm$^2$, preferred gap size of device is in the range of 2 um to 5 um, 5 um to 10 um, 10 um to 30 um, 30 um to 50 um thereby the counting and differentiate accuracy is less than 10%.

CC20. The device or method of any prior embodiments, wherein the spacer has a height in the range of 2 um to 5 um, thereby the WBCs missing counting is less than 15%.

CC21. The device or method of any prior embodiments, wherein the spacer has a height in the range of 2 um to 5 um, 5 um to 10 um, thereby the WBCs missing counting is less than 30%.

CC22. The device or method of any prior embodiments, wherein the spacer has a height of preferred range of 2 um to 5 um, 5 um to 10 um, 10 um to 30 um thereby the WBCs missing counting is less than 60%.

CC23. The device or method of any prior embodiments, wherein the sample to phone lens distance is in the range of 2 mm to 5 mm.

CC24. The device or method of any prior embodiments, wherein the sample to phone lens distance is in the range of 4 mm to 7 mm.

CC25. The device or method of any prior embodiments, wherein the sample to phone lens distance is in the range of 6 mm to 9 mm.

CC26. The device or method of any prior embodiments, wherein the sample to phone lens distance is in the range of 8 mm to 11 mm.

CC27. The device or method of any prior embodiments, wherein the sample to phone lens distance is in the range of 10 mm to 13 mm.

CC28. The device or method of any prior embodiments, wherein the sample to phone lens distance is in the range of 12 mm to 15 mm.

Additional Examples of Blood Cell Counting

A device for analyzing white blood cells in a blood sample, comprising:
 a first plate, a second plate, spacers, and adaptor wherein:
  i. the plates are movable relative to each other into different configurations;
  ii. one or both plates are flexible;
  iii. each of the plates comprises an inner surface that has a sample contact area for contacting a fluidic sample;
  iv. one or both of the plates comprise the spacers that are permanently fixed on the sample contact area of a respective plate;
  v. the spacers have:
   (a) a predetermined substantially uniform height that has a value selected in the range of 10 um to 50 um,
   (b) a shape of pillar with substantially uniform cross-section and a flat top surface;
   (c) a ratio of the width to the height equal or larger than one;
   (d) a predetermined fixed, non-random, inter-spacer distance that is in the range of 10 um to 200 um;
   (e) a filling factor of equal to 3% or larger, wherein the filling factor is the ratio of the spacer contact area (on the plate) to the total plate area; and
   (f) the filling factor multiplies the Young's modulus of the spacer is equal to 2 MPa or larger;
  vi. one or both of the plates comprise the reagents that are coated on the sample contact area of a respective plate;
  vii. the reagents have at least one of the following: (a) a component to stain the WBC; (b) a component to make the RBC distribution uniform; (c) a component to lyse the RBC; (d) a component to dilute the blood;
  viii. the adaptor comprises: (a) a housing, (b) an attachment member on the housing that allows the adaptor to be attached to a mobile phone with a camera, (c) a slot in the housing that allows (1) the plates in a closed configuration to slide into the slot and (2) when the plates are in the slot, at least a part of the sample area is less than 2 cm away from the outer surface of the camera, and (d) an optical system in the housing configured to have at least a part of the sample contact area be imaged by the camera;

wherein one of the configurations is an open configuration, in which: the two plates are partially or completely separated apart, the spacing between the plates is not regulated by the spacers, and the sample is deposited on one or both of the plates;

wherein another of the configurations is a closed configuration which is configured after the sample is deposited in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

A device for analyzing Hemoglobin in a blood sample, comprising:
  a first plate, a second plate, spacers, and adaptor wherein:
  i. the plates are movable relative to each other into different configurations;
  ii. one or both plates are flexible;
  iii. each of the plates comprises an inner surface that has a sample contact area for contacting a fluidic sample;
  iv. one or both of the plates comprise the spacers that are permanently fixed on the sample contact area of a respective plate;
  v. the spacers have:
    (a) a predetermined substantially uniform height that has a value selected in the range of 10 um to 50 um,
    (b) a shape of pillar with substantially uniform cross-section and a flat top surface;
    (c) a ratio of the width to the height equal or larger than one;
    (d) a predetermined fixed, non-random, inter-spacer distance that is in the range of 10 um to 200 um;
    (e) a filling factor of equal to 3% or larger, wherein the filling factor is the ratio of the spacer contact area (on the plate) to the total plate area; and
    (f) the filling factor multiplies the Young's modulus of the spacer is equal to 2 MPa or larger;
  vi. one or both of the plates comprise the reagents that are coated on the sample contact area of a respective plate;
  vii. the reagents have at least one of the following: (a) a component to make the RBC distribution uniform; (b) a component to lyse the RBC; (c) a component to dilute the blood;
  viii. the adaptor comprises: (a) a housing, (b) an attachment member on the housing that allows the adaptor to be attached to a mobile phone with a camera, (c) a slot in the housing that allows (1) the plates in a closed configuration to slide into the slot and (2) when the plates are in the slot, at least a part of the sample area is less than 2 cm away from the outer.

wherein one of the configurations is an open configuration, in which: the two plates are partially or completely separated apart, the spacing between the plates is not regulated by the spacers, and the sample is deposited on one or both of the plates;

wherein another of the configurations is a closed configuration which is configured after the sample is deposited in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

A device for analyzing red blood cell in a blood sample, comprising:
  a first plate, a second plate, spacers, and adaptor wherein:
  i. the plates are movable relative to each other into different configurations;
  ii. one or both plates are flexible;
  iii. each of the plates comprises an inner surface that has a sample contact area for contacting a fluidic sample;
  iv. one or both of the plates comprise the spacers that are permanently fixed on the sample contact area of a respective plate;
  v. the spacers have:
    (a) a predetermined substantially uniform height that has a value selected in the range of 1.5 um to 8 um,
    (b) a shape of pillar with substantially uniform cross-section and a flat top surface;
    (c) a ratio of the width to the height equal or larger than one;
    (d) a predetermined fixed, non-random, inter-spacer distance that is in the range of 10 um to 200 um;
    (e) a filling factor of equal to 3% or larger, wherein the filling factor is the ratio of the spacer contact area (on the plate) to the total plate area; and
    (f) the filling factor multiplies the Young's modulus of the spacer is equal to 2 MPa or larger;
  vi. one or both of the plates comprise the reagents that are coated on the sample contact area of a respective plate;
  vii. the reagents have at least one of the following: (a) a component to make the RBC distribution uniform; (b) a component to reduce the aggregation of RBC; (c) a component to stain the RBC; (d) a component to dilute the blood;
  viii. the adaptor comprises: (a) a housing, (b) an attachment member on the housing that allows the adaptor to be attached to a mobile phone with a camera, (c) a slot in the housing that allows (1) the plates in a closed configuration to slide into the slot and (2) when the plates are in the slot, at least a part of the sample area is less than 2 cm away from the outer.

wherein one of the configurations is an open configuration, in which: the two plates are partially or completely separated apart, the spacing between the plates is not regulated by the spacers, and the sample is deposited on one or both of the plates;

wherein another of the configurations is a closed configuration which is configured after the sample is deposited in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

A device for analyzing platelets in a blood sample, comprising:
  a first plate, a second plate, spacers, and adaptor wherein:
  i. the plates are movable relative to each other into different configurations;
  ii. one or both plates are flexible;
  iii. each of the plates comprises an inner surface that has a sample contact area for contacting a fluidic sample;
  iv. one or both of the plates comprise the spacers that are permanently fixed on the sample contact area of a respective plate;

v. the spacers have:
  (a) a predetermined substantially uniform height that has a value selected in the range of 1.5 um to 30 um;
  (b) a shape of pillar with substantially uniform cross-section and a flat top surface;
  (c) a ratio of the width to the height equal or larger than one;
  (d) a predetermined fixed, non-random, inter-spacer distance that is in the range of 10 um to 200 um;
  (e) a filling factor of equal to 3% or larger, wherein the filling factor is the ratio of the spacer contact area (on the plate) to the total plate area; and
  (f) the filling factor multiplies the Young's modulus of the spacer is equal to 2 MPa or larger;
vi. one or both of the plates comprise the reagents that are coated on the sample contact area of a respective plate;
vii. the reagents have at least one of the following: (a) a component to make the PLT distribution uniform; (b) a component to reduce the aggregation of PLT; (c) a component to stain the PLT; (d) a component to dilute the blood;
viii. the adaptor comprises: (a) a housing, (b) an attachment member on the housing that allows the adaptor to be attached to a mobile phone with a camera, (c) a slot in the housing that allows (1) the plates in a closed configuration to slide into the slot and (2) when the plates are in the slot, at least a part of the sample area is less than 2 cm away from the outer.

wherein one of the configurations is an open configuration, in which: the two plates are partially or completely separated apart, the spacing between the plates is not regulated by the spacers, and the sample is deposited on one or both of the plates;

wherein another of the configurations is a closed configuration which is configured after the sample is deposited in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

Spacer:

According to the present invention, the spacing between the two plates and hence the sample thickness are controlled by using the spacers.

Spacer height. In some embodiments, all spacers have the same pre-determined height. In some embodiments, spacers have different pre-determined heights. In some embodiments, spacers can be divided into groups or regions, wherein each group or region has its own spacer height. And in certain embodiments, the predetermined height of the spacers is an average height of the spacers. In some embodiments, the spacers have approximately the same height. In some embodiments, a percentage of number of the spacers have the same height.

The height of the spacers is selected by a desired regulated spacing between the plates and/or a regulated final sample thickness and the residue sample thickness. The spacer height (the predetermined spacer height), the spacing between the plates, and/or sample thickness is 3 nm or less, 10 nm or less, 50 nm or less, 100 nm or less, 200 nm or less, 500 nm or less, 800 nm or less, 1000 nm or less, 1 μm or less, 2 μm or less, 3 μm or less, 5 μm or less, 10 μm or less, 20 μm or less, 30 μm or less, 50 μm or less, 100 μm or less, 150 μm or less, 200 μm or less, 300 μm or less, 500 μm or less, 800 μm or less, 1 mm or less, 2 mm or less, 4 mm or less, or in a range between any two of the values.

The spacer height, the spacing between the plates, and/or sample thickness is between 1 nm to 100 nm in one preferred embodiment, 100 nm to 500 nm in another preferred embodiment, 500 nm to 1000 nm in a separate preferred embodiment, 1 μm (i.e. 1000 nm) to 2 μm in another preferred embodiment, 2 μm to 3 μm in a separate preferred embodiment, 3 μm to 5 μm in another preferred embodiment, 5 μm to 10 μm in a separate preferred embodiment, and 10 μm to 50 μm in another preferred embodiment, 50 μm to 100 μm in a separate preferred embodiment.

The spacer height, the spacing between the plates, and/or sample thickness is between 1.5 um to 2.5 um in one preferred embodiment.

The spacer height, the spacing between the plates, and/or sample thickness is between 2.5 um to 4 um in one preferred embodiment.

The spacer height, the spacing between the plates, and/or sample thickness is between 4 um to 6 um in one preferred embodiment.

The spacer height, the spacing between the plates, and/or sample thickness is between 6 um to 10 um in one preferred embodiment.

The spacer height, the spacing between the plates, and/or sample thickness is between 10 um to 15 um in one preferred embodiment.

The spacer height, the spacing between the plates, and/or sample thickness is between 15 um to 25 um in one preferred embodiment.

The spacer height, the spacing between the plates, and/or sample thickness is between 25 um to 35 um in one preferred embodiment.

The spacer height, the spacing between the plates, and/or sample thickness is between 35 um to 50 um in one preferred embodiment.

The spacer height, the spacing between the plates, and/or sample thickness is between 50 um to 100 um in one preferred embodiment.

The spacer height, the spacing between the plates, and/or sample thickness is between 100 um to 150 um in one preferred embodiment.

The spacer height, the spacing between the plates, and/or sample thickness is between 150 um to 200 um in one preferred embodiment.

The spacer height is related to and limited by the incident light source power density when testing the whole blood sample.

In one preferred embodiment, with incident light source power of 0.1 $W/cm^2$ to 5 $W/cm^2$, the spacer height, the spacing between the plates, and/or sample thickness is less than 2 um, less than 5 um, less than 10 um in one preferred embodiment.

In one preferred embodiment, with incident light source power of 0.1 $W/cm^2$ to 5 $W/cm^2$, the spacer height, the spacing between the plates, and/or sample thickness is less than 10 um, less than 20 um, less than 30 um in one preferred embodiment.

In one preferred embodiment, with incident light source power of 0.1 $W/cm^2$ to 5 $W/cm^2$, the spacer height, the spacing between the plates, and/or sample thickness is less than 30 um, less than 40 um, less than 50 um in one preferred embodiment.

In one preferred embodiment, with incident light source power of 5 $W/cm^2$ to 50 $W/cm^2$, the spacer height, the spacing between the plates, and/or sample thickness is less than 10 um, less than 20 um, less than 30 um in one preferred embodiment.

In one preferred embodiment, with incident light source power of 5 W/cm² to 50 W/cm², the spacer height, the spacing between the plates, and/or sample thickness is less than 30 um, less than 40 um, less than 50 um in one preferred embodiment.

In one preferred embodiment, with incident light source power of 5 W/cm² to 50 W/cm², the spacer height, the spacing between the plates, and/or sample thickness is less than 50 um, less than 100 um, less than 150 um, less than 200 um in one preferred embodiment.

In one preferred embodiment, with incident light source power of 50 W/cm² to 500 W/cm², the spacer height, the spacing between the plates, and/or sample thickness is less than 50 um, less than 100 um, less than 150 um, less than 200 um in one preferred embodiment.

In some embodiments, the spacer height is controlled precisely. The relative precision of the spacer (i.e. the ratio of the deviation to the desired spacer height) is 0.001% or less, 0.01% or less, 0.1% or less; 0.5% or less, 1% or less, 2% or less, 5% or less, 8% or less, 10% or less, 15% or less, 20% or less, 30% or less, 40% or less, 50% or less, 60% or less, 70% or less, 80% or less, 90% or less, 99.9% or less, or in a range between any of the values.

In some embodiments, the spacer height, the spacing between the plates, and/or sample thickness is: (i) equal to or slightly larger than the minimum dimension of an analyte, or (ii) equal to or slightly larger than the maximum dimension of an analyte. The "slightly larger" means that it is about 1% to 5% larger and any number between the two values.

In some embodiments, the spacer height, the spacing between the plates, and/or sample thickness is larger than the minimum dimension of an analyte (e.g. an analyte has an anisotropic shape), but less than the maximum dimension of the analyte.

For example, the red blood cell has a disk shape with a minim dimension of 2 μm (disk thickness) and a maximum dimension of 11 μm (a disk diameter). In an embodiment of the present invention, the spacers are selected to make the inner surface spacing of the plates in a relevant area to be 2 μm (equal to the minimum dimension) in one embodiment, 2.2 μm in another embodiment, or 3 (50% larger than the minimum dimension) in other embodiment, or 5 in other embodiment, but less than the maximum dimension of the red blood cell. Such embodiment has certain advantages in blood cell counting. In one embodiment, for red blood cell counting, by making the inner surface spacing at 2 or 6 μm and any number between the two values, an undiluted whole blood sample is confined in the spacing; on average, each red blood cell (RBC) does not overlap with others, allowing an accurate counting of the red blood cells visually. (Too many overlaps between the RBC's can cause serious errors in counting).

For example, the white blood cell has a dimension of 5 um to 20 um. In an embodiment of the present invention, the spacers are selected to make the inner surface spacing of the plates in a relevant area to be 5 μm (equal to the minimum dimension) in one embodiment, 10 μm in another embodiment, or 30 (50% larger than the minimum dimension) in other embodiment, or 5 in other embodiment, but less than the maximum dimension of the white blood cell. Such embodiment has certain advantages in blood cell counting. In one embodiment, for white blood cell counting, by making the inner surface spacing at 5 or 30 μm and any number between the two values, an undiluted whole blood sample is confined in the spacing, allowing an accurate counting of the red blood cells visually.

In some embodiments, the spacer height, the spacing between the plates, and/or sample thickness is: (i) equal to or smaller than the minimum dimension of an analyte, or (ii) equal to or slightly smaller than the maximum dimension of an analyte. The "slightly smaller" means that it is about 1% to 5% smaller and any number between the two values.

In some embodiments, the spacer height, the spacing between the plates, and/or sample thickness is larger than the minimum dimension of an analyte (e.g. an analyte has an anisotropic shape), but less than the maximum dimension of the analyte.

In the present invention, in some embodiments, the plates and the spacers are used to regulate not only the thickness of a sample, but also the orientation and/or surface density of the analytes/entity in the sample when the plates are at the closed configuration. When the plates are at a closed configuration, a thinner thickness of the sample results in less analytes/entity per surface area (i.e. less surface concentration).

Spacer lateral dimension. For an open-spacer, the lateral dimensions can be characterized by its lateral dimension (sometimes called width) in the x and y—two orthogonal directions. The lateral dimension of a spacer in each direction is the same or different. In some embodiments, the lateral dimension for each direction (x or y) is 1 nm or less, 3 nm or less, 5 nm or less, 7 nm or less, 10 nm or less, 20 nm or less, 30 nm or less, 40 nm or less, 50 nm or less, 100 nm or less, 200 nm or less, 500 nm or less, 800 nm or less, 1000 nm or less, 1 μm or less, 2 μm or less, 3 μm or less, 5 μm or less, 10 μm or less, 20 μm or less, 30 μm or less, 50 μm or less, 100 μm or less, 150 μm or less, 200 μm or less, 300 μm or less, or 500 μm or less, or in a range between any two of the values.

In some embodiments, the lateral dimension of a spacer is between 5 um and 10 um.

In some embodiments, the lateral dimension of a spacer is between 10 um and 15 um.

In some embodiments, the lateral dimension of a spacer is between 15 um and 20 um.

In some embodiments, the lateral dimension of a spacer is between 20 um and 25 um.

In some embodiments, the lateral dimension of a spacer is between 25 um and 30 um.

In some embodiments, the lateral dimension of a spacer is between 30 um and 40 um.

In some embodiments, the lateral dimension of a spacer is between 40 um and 50 um.

In some embodiments, the lateral dimension of a spacer is between 50 um and 70 um.

In some embodiments, the lateral dimension of a spacer is between 70 um and 90 um.

In some embodiments, the lateral dimension of a spacer is between 90 um and 120 um.

In some embodiments, the lateral dimension of a spacer is between 20 times and 40 times of the central wavelength of the incident light.

In some embodiments, the lateral dimension of a spacer is between 40 times and 80 times of the central wavelength of the incident light.

In some embodiments, the lateral dimension of a spacer is between 80 times and 120 times of the central wavelength of the incident light.

In some embodiments, the lateral dimension of a spacer is between 120 times and 80 times of the central wavelength of the incident light.

In some embodiments, the ratio of the lateral dimensions of x to y direction is 1, 1.5, 2, 5, 10, 100, 500, 1000, 10,000, or in a range between any two of the value. In some embodiments, a different ratio is used to regulate the sample flow direction; the larger the ratio, the flow is along one direction (larger size direction).

In some embodiments, different lateral dimensions of the spacers in x and y direction are used as (a) using the spacers as scale-markers to indicate the orientation of the plates, (b) using the spacers to create more sample flow in a preferred direction, or both.

In a preferred embodiment, the period, width, and height of the spacers are substantially the same. In some embodiments, all spacers have the same shape and dimensions. In some embodiments, the spacers have different lateral dimensions.

For enclosed-spacers, in some embodiments, the inner lateral shape and size are selected based on the total volume of a sample to be enclosed by the enclosed spacer(s), wherein the volume size has been described in the present disclosure; and in certain embodiments, the outer lateral shape and size are selected based on the needed strength to support the pressure of the liquid against the spacer and the compress pressure that presses the plates.

In certain embodiments, the aspect ratio of the height to the average lateral dimension of the pillar spacer is 100,000, 10,000, 1,000, 100, 10, 1, 0.1, 0.01, 0.001, 0.0001, 0, 00001, or in a range between any two of the values.

Inter-spacer distance. The spacers can be a single spacer or a plurality of spacers on the plate or in a relevant area of the sample. In some embodiments, the spacers on the plates are configured and/or arranged in an array form, and the array is a periodic, non-periodic array or periodic in some locations of the plate while non-periodic in other locations.

In some embodiments, the periodic array of the spacers is arranged as lattices of square, rectangle, triangle, hexagon, polygon, or any combinations of thereof, where a combination means that different locations of a plate has different spacer lattices.

In some embodiments, the inter-spacer distance of a spacer array is periodic (i.e. uniform inter-spacer distance) in at least one direction of the array. In some embodiments, the inter-spacer distance is configured to improve the uniformity between the plate spacing at a closed configuration.

In some embodiments, the distance between neighboring spacers (i.e. the inter-spacer distance) is 1 μm or less, 5 μm or less, 7 μm or less, 10 μm or less, 20 μm or less, 30 μm less, 40 μm or less, 50 μm or less, 60 μm or less, 70 μm or less, 80 μm or less, 90 μm or less, 100 μm or less, 200 μm or less, 300 μm or less, 400 μm or less, or in a range between any two of the values.

In certain embodiments, the inter-spacer distance is at 400 μm or less, 500 μm or less, 1 mm or less, 2 mm or less, 3 mm or less, 5 mm or less, 7 mm or less, 10 mm or less, or in any range between the values. In certain embodiments, the inter-spacer distance is a 10 mm or less, 20 mm or less, 30 mm or less, 50 mm or less, 70 mm or less, 100 mm or less, or in any range between the values.

The distance between neighboring spacers (i.e. the inter-spacer distance) is selected so that for a given properties of the plates and a sample, at the closed-configuration of the plates, the sample thickness variation between two neighboring spacers is, in some embodiments, at most 0.5%, 1%, 5%, 10%, 20%, 30%, 50%, 80%, or in any range between the values; or in certain embodiments, at most 80%, 100%, 200%, 400%, or in a range between any two of the values.

Clearly, for maintaining a given sample thickness variation between two neighboring spacers, when a more flexible plate is used, a closer inter-spacer distance is needed.

In a preferred embodiment, the inter-spacer spacing is between 20 um and 50 um.

In a preferred embodiment, the inter-spacer spacing is between 50 um and 80 um.

In a preferred embodiment, the inter-spacer spacing is between 80 um and 100 um.

In a preferred embodiment, the inter-spacer spacing is between 100 um and 150 um.

In a preferred embodiment, the inter-spacer spacing is between 150 um and 200 um.

In a preferred embodiment, the inter-spacer spacing is between 200 um and 250 um.

In a preferred embodiment, the inter-spacer spacing is between 250 um and 300 um.

In a preferred embodiment, the inter-spacer spacing is between 300 um and 400 um.

In a preferred embodiment, the inter-spacer spacing is between 400 um and 500 um.

In a preferred embodiment, the spacer is a periodic square array, wherein the spacer is a pillar that has a height of 2 to 6 μm, an average lateral dimension of from 10 to 40 μm, and inter-spacer spacing of 1 μm to 100 μm.

In a preferred embodiment, the spacer is a periodic square array, wherein the spacer is a pillar that has a height of 2 to 6 μm, an average lateral dimension of from 10 to 50 μm, and inter-spacer spacing of 100 μm to 250 μm.

In a preferred embodiment, the spacer is a periodic square array, wherein the spacer is a pillar that has a height of 10 to 50 μm, an average lateral dimension of from 20 to 50 μm, and inter-spacer spacing of 1 μm to 100 μm.

In a preferred embodiment, the spacer is a periodic square array, wherein the spacer is a pillar that has a height of 10 to 50 μm, an average lateral dimension of from 20 to 50 μm, and inter-spacer spacing of 100 μm to 250 μm.

The period of spacer array is between 1 nm to 100 nm in one preferred embodiment, 100 nm to 500 nm in another preferred embodiment, 500 nm to 1000 nm in a separate preferred embodiment, 1 μm (i.e. 1000 nm) to 2 μm in another preferred embodiment, 2 μm to 3 μm in a separate preferred embodiment, 3 μm to 5 μm in another preferred embodiment, 5 μm to 10 μm in a separate preferred embodiment, and 10 μm to 50 μm in another preferred embodiment, 50 μm to 100 μm in a separate preferred embodiment, 100 μm to 175 μm in a separate preferred embodiment, and 175 μm to 300 μm in a separate preferred embodiment.

Spacer density. The spacers are arranged on the respective plates at a surface density of greater than one per $\mu m^2$, greater than one per 10 $\mu m^2$, greater than one per 100 $\mu m^2$, greater than one per 500 $\mu m^2$, greater than one per 1000 $\mu m^2$, greater than one per 5000 $\mu m^2$, greater than one per 0.01 $mm^2$, greater than one per 0.1 $mm^2$, greater than one per 1 $mm^2$, greater than one per 5 $mm^2$, greater than one per 10 $mm^2$, greater than one per 100 $mm^2$, greater than one per 1000 $mm^2$, greater than one per 10000 $mm^2$, or in a range between any two of the values. In some embodiments, the spacers have a density of at least $1/mm^2$, at least $10/mm^2$, at least $50/mm^2$, at least $100/mm^2$, at least $1,000/mm^2$, or at least $10,000/mm^2$.

Spacer area filling factor is defined as the ratio of spacer area to the total area or the ratio of spacer period to the width. In some embodiments, the filling factor is at least 1%, 2%, 3%, 4%, 5%, 6%, 7%, 8%, 9%, 10%, 20%, or in the range between any of the two values. In certain embodiments, the filling factor is at least 2.3%.

The device that comprises two plates and spacers, wherein the fourth power of the inter-spacer-distance (ISD)

divided by the thickness (h) and the Young's modulus (E) of the flexible plate (ISD^4/(hE)) is 5×10^6 um^3/GPa or less.

The device that comprises two plates and spacers, wherein the fourth power of the inter-spacer-distance (ISD) divided by the thickness (h) and the Young's modulus (E) of the flexible plate (ISD^4/(hE)) is 5×10^5 um3/GPa or less.

The device that comprises two plates and spacers, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one).

The device that comprises two plates and spacers, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one), wherein the fourth power of the inter-spacer-distance (ISD) divided by the thickness (h) and the Young's modulus (E) of the flexible plate (ISD^4/(hE)) is 5×10^6 um^3/GPa or less.

The device that comprises two plates and spacers, wherein the ratio of the inter-spacing distance of the spacers to the average width of the spacer is 2 or larger, and the filling factor of the spacers multiplied by the Young's modulus of the spacers is 2 MPa or larger.

Area, Width and Length of the Card:

The device, kit, system, or method of any prior embodiments, wherein the area of any one of the plates depends on the specific application.

The device, kit, system, or method of any prior embodiments, wherein the area of at least one of the plate is 1 mm$^2$ (square millimeter) or less, 10 mm$^2$ or less, 25 mm$^2$ or less, 50 mm$^2$ or less, 75 mm$^2$ or less, 1 cm$^2$ (square centimeter) or less, 2 cm$^2$ or less, 3 cm$^2$ or less, 4 cm$^2$ or less, 5 cm$^2$ or less, 10 cm$^2$ or less, 100 cm$^2$ or less, 500 cm$^2$ or less, 1000 cm$^2$ or less, 5000 cm$^2$ or less, 10,000 cm$^2$ or less, 10,000 cm$^2$ or less, or in a range between any of the two values.

The device, kit, system, or method of any prior embodiments, wherein the area of at least one plate of the QMAX card is in the range of 500 to 1000 mm$^2$;

The device, kit, system, or method of any prior embodiments, wherein the area of one plate is around 600 mm$^2$ and the area of another plate is around 750 mm$^2$.

The device, kit, system, or method of any prior embodiments, wherein the width of at least one of the plates of the QMAX card is 1 mm or less, 5 mm or less, 10 mm or less, 15 mm or less, 20 mm or less, 25 mm or less, 30 mm or less, 35 mm or less, 40 mm or less, 45 mm or less, 50 mm or less, 100 mm or less, 200 mm or less, 500 mm or less, 1000 mm or less, 5000 mm or less, or in a range between any of the two values.

The device, kit, system, or method of any prior embodiments, wherein the width of at least one plate of the QMAX card is in the range of 20 mm to 30 mm;

The device, kit, system, or method of any prior embodiments, wherein the width of one plate is around 22 mm and the width of another plate is around 24 mm.

The device, kit, system, or method of any prior embodiments, wherein the length of at least one of the plates of the QMAX card is 1 mm or less, 5 mm or less, 10 mm or less, 15 mm or less, 20 mm or less, 25 mm or less, 30 mm or less, 35 mm or less, 40 mm or less, 45 mm or less, 50 mm or less, 100 mm or less, 200 mm or less, 500 mm or less, 1000 mm or less, 5000 mm or less, or in a range between any of the two values.

The device, kit, system, or method of any prior embodiments, wherein the length of at least one plate of the QMAX card is in the range of 20 to 40 mm;

The device, kit, system, or method of any prior embodiments, wherein the length of one plate is around 27 mm and the length of another plate is around 32 mm.

The device, kit, system, or method of any prior embodiments, wherein the length of one plate is around 27 mm and the width of this plate is around 22 mm.

The device, kit, system, or method of any prior embodiments, wherein the length of one plate is around 32 mm and the width of this plate is around 24 mm.

The device, kit, system, or method of any prior embodiments, wherein the length of one plate is around 27 mm and the length of another plate is around 32 mm, and the width of one plate is around 22 mm and the width of another plate is around 24 mm.

Shape of the Card:

The device, kit, system, or method of any prior embodiments, wherein the shape of the two plates is round, ellipse, rectangle, triangle, polygonal, ring-shaped, or any superposition of these shapes.

The device, kit, system, or method of any prior embodiments, wherein the two (or more) plates of the QMAX card can have the same size and/or shape, or different size and/or shape.

The device, kit, system, or method of any prior embodiments, wherein the two (or more) plates of the QMAX card has round corners for user safety concerns, wherein the round corners have a diameter of 100 um or less, 200 um or less, 500 um or less, 1 mm or less, 2 mm or less, 5 mm or less, 10 mm or less, 50 mm or less, or in a range between any two of the values.

The device, kit, system, or method of any prior embodiments, wherein the plates can have any shape, preferably, a shape that allows a compress open flow of the sample and the regulation of the sample thickness.

The device, kit, system, or method of any prior embodiments, wherein the particular shape of the plates is advantageous.

Thickness of the Card:

The device, kit, system, or method of any prior embodiments, wherein the thickness, width, and/or length of the two (or more) plates of the QMAX card can be the same or different.

The device, kit, system, or method of any prior embodiments, wherein the average thickness for at least one of the plates is 2 nm or less, 10 nm or less, 100 nm or less, 200 nm or less, 500 nm or less, 1000 nm or less, 2 μm (micron) or less, 5 μm or less, 10 μm or less, 20 μm or less, 50 μm or less, 100 μm or less, 150 μm or less, 200 μm or less, 300 μm or less, 500 μm or less, 800 μm or less, 1 mm (millimeter) or less, 2 mm or less, 3 mm or less, 5 mm or less, 10 mm or less, 20 mm or less, 50 mm or less, 100 mm or less, 500 mm or less, or in a range between any two of the values.

The device, kit, system, or method of any prior embodiments, wherein the thickness of at least one of the plates is in the range of 0.5 to 1.5 mm; The device, kit, system, or method of any prior embodiments, wherein the thickness of at least one of the plates is around 1 mm.

The device, kit, system, or method of any prior embodiments, wherein the thickness of at least one of the plates is in the range of 0.15 to 0.2 mm.

The device, kit, system, or method of any prior embodiments, wherein the thickness of at least one of the plates is around 0.175 mm.

The device, kit, system, or method of any prior embodiments, wherein the thickness of at least one of the plates is in the range of 0.01 to 0.15 mm.

The device, kit, system, or method of any prior embodiments, wherein the thickness of at least one of the plates is around 0.025 mm.

The device, kit, system, or method of any prior embodiments, wherein the thickness of at least one of the plates is around 0.05 mm.

The device, kit, system, or method of any prior embodiments, wherein the thickness of at least one of the plates is around 0.1 mm.

The device, kit, system, or method of any prior embodiments, wherein the thickness of any one of the plates is not uniform across the plate.

The device, kit, system, or method of any prior embodiments, wherein a different plate thickness at different location can be used to control the plate bending, folding, sample thickness regulation, and others.

Notch:

The device, kit, system, or method of any prior embodiments, wherein the notch or multi-notches are on the side(s) of one of the plates for easily peeling up the other plate and separate the two plates.

The device, kit, system, or method of any prior embodiments, wherein the shape of the notch is round, ellipse, rectangle, triangle, polygon, ring-shaped, or any superposition of these shapes.

The device, kit, system, or method of any prior embodiments, wherein the size of the notch is 1 mm$^2$ (square millimeter) or less, 10 mm$^2$ or less, 25 mm$^2$ or less, 50 mm$^2$ or less, 75 mm$^2$ or less or in a range between any of the two values.

The device, kit, system, or method of any prior embodiments, wherein the area of each notch on the QMAX card is in the range of 10 to 30 mm$^2$.

The device, kit, system, or method of any prior embodiments, wherein the notch is half-round shape with a diameter of 3 to 6 mm.

The device, kit, system, or method of any prior embodiments, wherein the notch has a width of 3 mm and a length of 6 mm.

The device, kit, system, or method of any prior embodiments, wherein the notch locates at the short width side on the thicker plate.

The device, kit, system, or method of any prior embodiments, wherein the two notches are located at the two long width sides of the thicker plate.

Hinge:

The device, kit, system, or method of any prior embodiments, wherein the size of the hinge vary and can be adjusted according to the size of the plates and the specific needs of the application for the device.

The device, kit, system, or method of any prior embodiments, wherein the shape of the hinge is round, ellipse, rectangle, triangle, polygon, ring-shaped, or any superposition of these shapes.

The device, kit, system, or method of any prior embodiments, wherein the length of the hinge joint is less than 1 mm, 2 mm, 3 mm, 4 mm, 5 mm, 10 mm, 15 mm, 20 mm, 25 mm, 30 mm, 40 mm, 50 mm, 100 mm, 200 mm, or 500 mm, or in a range between any of the two values.

The device, kit, system, or method of any prior embodiments, wherein the length of the hinge joint is around 20 mm.

The device, kit, system, or method of any prior embodiments, wherein the width of the hinge joint is less than 1 mm, 2 mm, 3 mm, 4 mm, 5 mm, 10 mm, 15 mm, 20 mm, 25 mm, 30 mm, 40 mm, 50 mm, 100 mm, 200 mm, or 500 mm, or in a range between any of the two values.

The device, kit, system, or method of any prior embodiments, wherein the width of the hinge joint is around 6 mm.

The device, kit, system, or method of any prior embodiments, wherein the length of the hinge joint is around 20 mm and the width of the hinge joint is around 6 mm.

The device, kit, system, or method of any prior embodiments, wherein the ratio of the length of the hinge joint to the length of the plate edge with which the hinge joint is aligned is less than 1.5, 1, 0.9, 0.8, 0.7, 0.6, 0.5, 0.4, 0.3, 0.2, 0.1, 0.05 or in a range between any two of these values.

The device, kit, system, or method of any prior embodiments, wherein the ratio of the length of the hinge joint to the length of the plate edge with which the hinge joint 36 is aligned is 1, indicating that the hinge joint completely covers the hinge edge.

The device, kit, system, or method of any prior embodiments, wherein the overall area of the hinge is less than 1 mm$^2$, 5 mm$^2$, 10 mm$^2$, 20 mm$^2$, 30 mm$^2$, 40 mm$^2$, 50 mm$^2$, 100 mm$^2$, 200 mm$^2$, 500 mm$^2$, or in a range between any of the two values.

The device, kit, system, or method of any prior embodiments, wherein the overall area of the hinge is around 120 mm$^2$.

The device, kit, system, or method of any prior embodiments, wherein the ratio of the overall size of the hinge to the overall size of one of the plates is less than 1, 0.9, 0.8, 0.7, 0.6, 0.5, 0.4, 0.3, 0.2, 0.1, 0.05, 0.01 or in a range between any two of these values.

The device, kit, system, or method of any prior embodiments, wherein the ratio of the overall size of the hinge to the overall size of one of the plates is around 0.16 to 0.20.

The device, kit, system, or method of any prior embodiments, wherein the different layers of the hinge has the same or different thickness.

The device, kit, system, or method of any prior embodiments, wherein any layer of the hinge has a thickness in 0.1 um, 1 um, 2 um, 3 um, 5 um, 10 um, 20 um, 30 um, 50 um, 100 um, 200 um, 300 um, 500 um, 1 mm, 2 mm, and a range between any two of these values.

The device, kit, system, or method of any prior embodiments, wherein any of the layers of hinge has a thickness in the range of 25 µm to 50 µm.

The device, kit, system, or method of any prior embodiments, wherein any of the layers of hinge has a thickness in the range of 50 µm to 75 µm.

The device, kit, system, or method of any prior embodiments, wherein any of the layers of hinge has a thickness around 68 µm.

The device, kit, system, or method of any prior embodiments, wherein the length of the hinge joint is around 20 mm, the width of the hinge joint is around 6 mm and the thickness of the hinge joint is around 68 µm.

Receptacle Slot:

The device, kit, system, or method of any prior embodiments, wherein the receiving area of the receptacle slot, or the lateral area covered by the sliding track has an area larger or equal as the area of the QMAX device.

The device, kit, system, or method of any prior embodiments, wherein the shape of the receiving area of the receptacle slot is round, ellipse, rectangle, triangle, polygon, ring-shaped, or any superposition of these shapes;

The device, kit, system, or method of any prior embodiments, wherein the average gap size of the sliding track is larger than the average thickness of the device by 100 nm, 500 nm, 1 um, 2 um, 5 um, 10 um, 50 um, 100 um, 300 um, 500 um, 1 mm, 2 mm, 5 mm, 1 cm, or in a range between any two of the values.

The device, kit, system, or method of any prior embodiments, wherein the average gap size of the slot is larger than the average thickness of the device by 50 um to 300 um.

The device, kit, system, or method of any prior embodiments, wherein the receiving area of the receptacle slot is larger than the area of the device by 1 mm$^2$ (square millimeter) or less, 10 mm$^2$ or less, 25 mm$^2$ or less, 50 mm$^2$ or less, 75 mm$^2$ or less, 1 cm$^2$ (square centimeter) or less, 2 cm$^2$ or less, 3 cm$^2$ or less, 4 cm$^2$ or less, 5 cm$^2$ or less, 10 cm$^2$ or less, 100 cm$^2$ or less, or in a range between any of the two values.

The device, kit, system, or method of any prior embodiments, wherein the shape of one of the plates or both of the plates is the same as the shape of the receptacle slot.

The device, kit, system, or method of any prior embodiments, wherein the receptacle slot has a shape of box with one open surface, with a length of 31 mm, a width of 27 mm and a height of 2.5 mm.

The device, kit, system, or method of any prior embodiments, wherein the QMAX device is only partially inside the receptacle slot at best when they are fully engaged, the shape of part of one of the plates or both of the plates is the same as the shape of the receptacle slot.

Reagent:

The device, kit, system, or method of any prior embodiments, wherein the dye to stain the WBC is coated onto the first plate, or the second plate or both.

The device, kit, system, or method of any prior embodiments, wherein the dye to stain the WBC and PLT is coated onto the first plate, or the second plate or both.

The device, kit, system, or method of any prior embodiments, wherein the dye to stain the PLT is coated onto the first plate, or the second plate or both.

The device, kit, system, or method of any prior embodiments, wherein the reagents is coated by droplet printing into an array.

The device, kit, system, or method of any prior embodiments, wherein the reagents is coated by spray.

The device, kit, system, or method of any prior embodiments, wherein the reagents is coated by contact printing.

The device, kit, system, or method of any prior embodiments, wherein the reagents is coated by transfer printing.

The device, kit, system, or method of any prior embodiments, wherein the dye to stain the RBC is coated onto the first plate, or the second plate or both.

The device, kit, system, or method of any prior embodiments, wherein the surfactant to separate and round RBC is coated onto the first plate, or the second plate or both.

The device, kit, system, or method of any prior embodiments, wherein the chemical to lyse RBC is coated onto the first plate, or the second plate or both.

The device, kit, system, or method of any prior embodiments, wherein the acridine orange is coated onto the first plate, or the second plate or both.

The device, kit, system, or method of any prior embodiments, wherein the Zwittergent is coated onto the first plate, or the second plate or both.

The device, kit, system, or method of any prior embodiments, wherein the Methylene blue and Zwittergent is coated onto the first plate, or the second plate or both.

The device, kit, system, or method of any prior embodiments, wherein the acridine orange and Zwittergent is coated onto the first plate, or the second plate or both.

The device, kit, system, or method of any prior embodiments, wherein the YOYO dye and Zwittergent is coated onto the first plate, or the second plate or both.

The devices or methods of any prior embodiment, wherein the device further comprises, on one or both plates, multi reagent layers including anti-conglutination, cell lysing, cell staining, release time control material layers, and their combinations;

wherein each layer coated on the plates has a thickness of 10 nm, 100 nm, 200 nm, 500 nm, 1 um or a range between any two of the values.

where anti-conglutination agent comprises ethylenediaminetetraacetic acid (EDTA), EDTA disodium, K2EDTA, K3EDTA, and etc.

wherein cell stain agent comprise Wright's stain (Eosin, methylene blue), Giemsa stain (Eosin, methylene blue, and Azure B), May-Grünwald stain, Leishman's stain ("Polychromed" methylene blue (i.e. demethylated into various azures) and eosin), Erythrosine B stain (Erythrosin B), and other fluorescence stain including but not limit to Acridine orange dye, 3,3-dihexyloxacarbocyanine (DiOC6), Propidium Iodide (PI), Fluorescein Isothiocyanate (FITC) and Basic Orange 21 (BO21) dye, Ethidium Bromide, Brilliant Sulfaflavine and a Stilbene Disulfonic Acid derivative, Erythrosine B or trypan blue, Hoechst 33342, Trihydrochloride, Trihydrate, and DAPI (4',6-Diamidino-2-Phenylindole, Dihydrochloride), YOYO.

wherein cell stain agent comprise Wright's stain (Eosin, methylene blue), Giemsa stain (Eosin, methylene blue, and Azure B), May-Grünwald stain, Leishman's stain ("Polychromed" methylene blue (i.e. demethylated into various azures) and eosin), Erythrosine B stain (Erythrosin B), and other fluorescence stain including but not limit to Acridine orange dye, 3,3-dihexyloxacarbocyanine (DiOC6), Propidium Iodide (PI), Fluorescein Isothiocyanate (FITC) and Basic Orange 21 (BO21) dye, Ethidium Bromide, Brilliant Sulfaflavine and a Stilbene Disulfonic Acid derivative, Erythrosine B or trypan blue, Hoechst 33342, Trihydrochloride, Trihydrate, and DAPI (4',6-Diamidino-2-Phenylindole, Dihydrochloride), YOYO, acid fuchsine, hematoxylin, Hoechst stains including Hoechst 33258 and Hoechst 33342, methyl green, methylene blue, Nile blue, Nile red, osmium tetraoxide, rhodamine, safranine, MeOSuc-AAPV-AMC, CFSE, BCECF/AM, silver nitrate, neutral red, pyronin Y, Calcein-AM, Dihydroethidium, Xylene Cyanol FF, Rhodamine 123, 4-Methylumbelliferyl palmitate, Fast Blue B Salt, Lucifer Yellow CH dipotassium salt, DAPI dilactate, Propidium Iodide;

wherein cell lysing agent comprise ammonium chloride, sodium bicarbonate, ethylenediaminetetraacetic acid (EDTA), acetic acid, citric acid, other acid and base, and etc.

wherein release time control material comprise albumin, carbomers, carboxymethyl cellulose, carrageenan, chitosan, dextrin, polyethylene glycol, polyvinylpyrrolidone, polyvinyl alcohol, and etc.

In some embodiment, chemicals with certain concentration is coated on the plate and dissolved into the blood to achieve a uniform distribution of red blood cell in device.

In some embodiment, chemicals with certain concentration is coated on the plate and dissolved into the blood to lyse the red blood cell in device, wherein the coating can be on first plate, or second plate, or both.

In some embodiment, the chemicals coated in the device including but not limit to Surfactant, Zwittergent, ASB-14, ASB-16, CHAPS, Cationic surfactant NN-[Tris(hydroxymethyl) methyl]-N-alkyl-N,N-dimethyl ammonium chloride (IIa), IIb, IIc, IId, CTAC, Tween 20, Tween 40, Tween 60, Tween 80, Sodium lauryl sulfate (SLS), ammonium lauryl sulfate, CTAB, sodium lauryl ether sulfate (SLES), sodium myreth sulfate, docusate, perfluorooctanesulfonate, alkylaryl ether phosphates, alkyl ether phosphates, CTAB, cetylpyridinium chloride (CPC), benzalkonium chloride (BAC), benzethonium chloride (BZT), dimethyldioctadecylammonium chloride, dioctadecyldimethylammonium bromide (DODAB), cocamidopropyl hydroxysultaine, cocamidopropyl betaine, narrow-range ethoxylate, octaethylene glycol monododecyl ether, pentaethylene glycol monododecyl ether, nonxynols, Triton X-100, polyethoxylated tallow amine, cocamide monoethanolamine, cocamide diethanolamine, poloxamers, glycerol monostearate, glycerol monolaurate, sorbitan monolaurate, sorbitan monostearate, sorbitan tristearate, decyl glucoside, lauryl glucoside, octyl glucoside, lauryldimethylamine oxide, dimethyl sulfoxide, phosphine oxide.

In some embodiment, the reagent causing red blood cell lysis coated in the device including but not limit to Pluronic F-127, Cremophor EL, Pluronic F-68, Myrj 52, Brij 35, sodium oleate, sodium dodecyl sulfate, Tween 20, Tween 40, Tween 60, Tween 80, SLS, CTAB, CTAC, Tamoxifen, saponin, hydrochloric acid, sulfuric acid, nitric acid, phosphoric acid, lactic acid, ABS-14, ABS-16, anti-malaria drugs (quinine compounds), arsenic, dapsone, metals (chromium/chromates, platinum salts, nickel compounds, copper, lead, cis-platinum), nitrites, nitrofurantoin, penicillin, phenazopyridine (pyridium), rho immune globulin, ribavirin, sulfonamides, sulfones.

In some embodiment, the anticoagulant coated in the device including but not limit to EDTA such as dipotassium ethylenediaminetetraacetic acid (K2EDTA), tripotassium ethylenediaminetetraacetic (K3EDTA), coumarins (vitamin K antagonists), warfarin (coumadin), acenocoumarol, phenprocoumon, atromentin, phenindione, heparin, fondaparinux and idraparinux, dabigatran, rivaroxaban, apixaban, edoxaban, betrixaban, NOACs, hirudin, lepirudin, bivalirudin, agratroban, dabigatran, batroxobin, hementin, Vitamin E, sodium citrate, acid citrate dextrose, oxalate such as fluoride oxalate, deltaparin, desirudin, enoxaparin.

In some embodiment, to achieve a uniform distribution of red blood cell in device, Zwittergent is coated on the plate with a preferred area concentration of 3 ng/mm2, 5 ng/mm2, 8 ng/mm2, 12 ng/mm2, 15 ng/mm2, 25 ng/mm2, 35 ng/mm2, 50 ng/mm2, 80 ng/mm2, 100 ng/mm2 or in a range between any of the two values.

In some embodiment, to lyse red blood cell in device, Zwittergent is coated on the plate with a preferred area concentration of 100 ng/mm2, 120 ng/mm2, 150 ng/mm2, 180 ng/mm2, 200 ng/mm2, 300 ng/mm2, 400 ng/mm2, 500 ng/mm2, 800 ng/mm2, 1000 ng/mm2 or in a range between any of the two values.

In some embodiment, to achieve a uniform distribution of red blood cell in device, Zwittergent is coated on the plate with a preferred final concentration in blood of 0.05 mg/mL, 0.1 mg/mL, 0.2 mg/mL, 0.3 mg/mL, 0.5 mg/mL, 0.6 mg/mL, 1.0 mg/mL, 2 mg/mL or in a range between any of the two values.

In some embodiment, to lyse red blood cell in device, Zwittergent is coated on the plate with a preferred final concentration in blood of 2 mg/mL, 3 mg/mL, 4 mg/mL, 5 mg/mL, 6 mg/mL, 7 mg/mL, 9 mg/mL, 10 mg/mL, 15 mg/mL, 25 mg/mL, 50 mg/mL, or in a range between any of the two values.

In some embodiment, to achieve a uniform distribution of red blood cell in device, Zwittergent is coated on the plate with a preferred area concentration of 3 ng/mm$^2$, 5 ng/mm$^2$, 8 ng/mm$^2$, 12 ng/mm$^2$, 15 ng/mm$^2$, 25 ng/mm$^2$, 35 ng/mm$^2$, 50 ng/mm$^2$, 80 ng/mm$^2$, 100 ng/mm$^2$ or in a range between any of the two values.

In some embodiment, to lyse red blood cell in device, Zwittergent is coated on the plate with a preferred area concentration of 100 ng/mm$^2$, 120 ng/mm$^2$, 150 ng/mm$^2$, 180 ng/mm$^2$, 200 ng/mm$^2$, 300 ng/mm$^2$, 400 ng/mm$^2$, 500 ng/mm$^2$, 800 ng/mm$^2$, 1000 ng/mm$^2$ or in a range between any of the two values.

In some embodiment, to achieve a uniform distribution of red blood cell in device, Zwittergent is coated on the plate with a preferred final concentration in blood of 0.05 mg/mL, 0.1 mg/mL, 0.2 mg/mL, 0.3 mg/mL, 0.5 mg/mL, 0.6 mg/mL, 1.0 mg/mL, 2 mg/mL or in a range between any of the two values.

In some embodiment, to lyse red blood cell in device, Zwittergent is coated on the plate with a preferred final concentration in blood of 2 mg/mL, 3 mg/mL, 4 mg/mL, 5 mg/mL, 6 mg/mL, 7 mg/mL, 9 mg/mL, 10 mg/mL, 15 mg/mL, 25 mg/mL, 50 mg/mL, or in a range between any of the two values.

The device, kit, system, or method of any prior embodiments, wherein the acridine orange is coated on the plate with an area concentration of 0.5 ng/mm$^2$, 1 ng/mm$^2$, 2 ng/mm$^2$, 3 ng/mm$^2$, 5 ng/mm$^2$, 8 ng/mm$^2$, 10 ng/mm$^2$, 15 ng/mm$^2$, 20 ng/mm$^2$, 30 ng/mm$^2$ or in a range between any of the two values.

The device, kit, system, or method of any prior embodiments, wherein the acridine orange is coated on the plate with an area concentration of 3 to 10 ng/mm$^2$ and Zwittergent is coated on the plate with an area concentration of 3 to 10 ng/mm$^2$.

The device, kit, system, or method of any prior embodiments, wherein the acridine orange is coated on the plate with an area concentration of 5 to 20 ng/mm$^2$ and Zwittergent is coated on the plate with an area concentration of 10 to 30 ng/mm$^2$.

Material:

The device, kit, system, or method of any prior embodiments, wherein the material of first place and second plate is Poly(methyl methacrylate), Polystyrene, polycarbonate, Polyethylene terephthalate, polyamides, polyester, polyethylene, polypropylene, polyurethanes, polyvinyl chloride, acrylonitrile butadiene styrene, polyepoxide, polyetrafluoroethylene, phenolic, furan, silicone, polylactic acid, polyimide and others.

The device, kit, system, or method of any prior embodiments, wherein the surface of first place and second plate is silicon oxide or silicon nitride.

The device, kit, system, or method of any prior embodiments, wherein the surface of first place and second plate is treated into hydrophilic.

The device, kit, system, or method of any prior embodiments, wherein the surface of first place and second plate is treated nonbinding for cell.

Transfer Tube:

The device, kit, system, or method of any prior embodiments, wherein the blood is transferred directly onto the QMAX card from finger.

The device, kit, system, or method of any prior embodiments, wherein the blood is transferred from a body surface onto the QMAX card using a transfer tube that has a volume of 2 uL, 3 uL, 5 uL, 8 uL, 10 uL, 15 uL or in a range between any of the two values.

Landing Mark:

The device, kit, system, or method of any prior embodiments, wherein a landing mark for blood droplet is on the outside surface of first plate or second plate.

The device, kit, system, or method of any prior embodiments, wherein a landing mark for blood droplet is outside the field of view of the image.

The device, kit, system, or method of any prior embodiments, wherein a landing mark for blood droplet is near the center of the card.

The device, kit, system, or method of any prior embodiments, wherein a landing mark for blood droplet is a small dot or a small cross.

Filling Mark:

The device, kit, system, or method of any prior embodiments, wherein a filling mark for notifying the user the minimum volume and cover area of sample in the device is on the outside surface of first plate or second plate.

The device, kit, system, or method of any prior embodiments, wherein a filling mark for notifying the user the minimum volume and cover area of sample in the device is outside the field of view of the image.

The device, kit, system, or method of any prior embodiments, wherein a filling mark for notifying the user the minimum volume and cover area of sample in the device is near the center of the card.

The device, kit, system, or method of any prior embodiments, wherein a filling mark for notifying the user the minimum volume and cover area of sample in the device is a circle or a rectangle.

Figure 7:
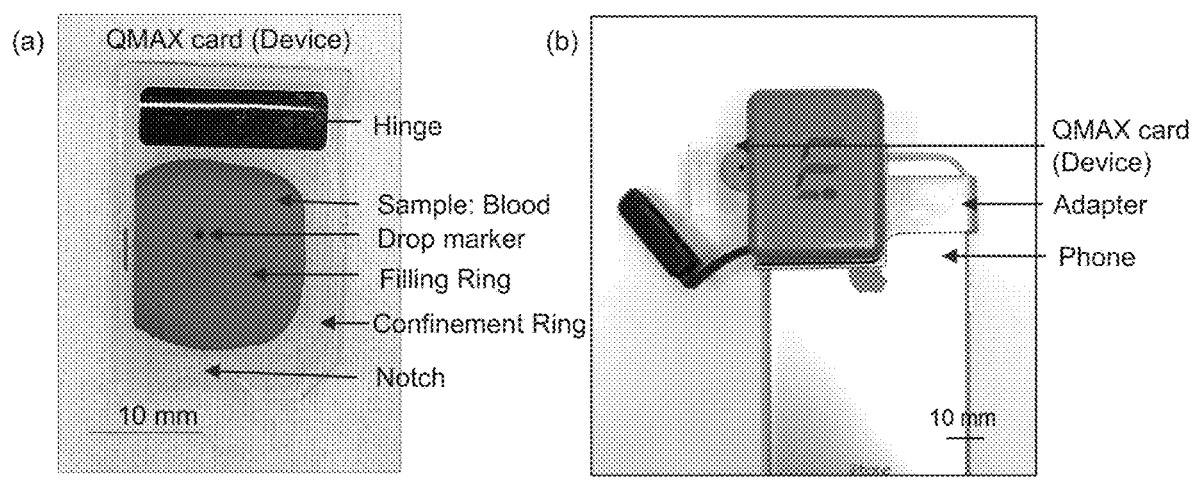
FIG. 7 shows the (a) the photo of one QMAX device and (b) the photo of QMAX device and adapter on a smartphone.

Example: QMAX Device Measure Complete Blood Count and Compare with Commercial Machine One example device and method using QMAX device to measure complete blood count (CBC) is shown in FIG. 7. The device is able to measure all the CBC parameters without dilution. The preliminary test shows the results using such device is accurate compared with commercial machine.

FIG. 7 shows the (a) the photo of one QMAX device and (b) the photo of QMAX device and adapter on a smartphone.

The device was fabricated with the materials of PMMA. The device can be fabricated with the materials of polystyrene, PMMA, PC, COC, COP, or another plastic.

The plate 1 used in the example has a thickness of 950 um to 1050 um. The plate 1 have a preferred thickness range of 200 um to 1500 um.

The plate 2 used in the example has a thickness of 170 um to 180 um. The plate 2 have a preferred thickness range of 50 um to 250 um.

One device to measure RBC and PLT in the experiment has a pillar height 5 um, inter pillar distance of 90 um, and a pillar size 20 um. The pillar can have a pillar height from 2 um to 6 um with a inter pillar distance of 50 um to 200 um and a pillar size 5 um to 40 um.

One device to measure HgB and WBC in the experiment has a pillar height 30 um, inter pillar distance of 80 um, and a pillar size 30 um. The pillar can have a pillar height from 20 um to 50 um with a inter pillar distance of 50 um to 200 um and a pillar size 10 um to 50 um.

The acridine orange dye for staining WBC and PLT, and the Zwittergent for distribute the RBC is coated on the plate 1.

The acridine orange is coated on the plate with an area concentration of 10 to 80 ng/mm$^2$ and Zwittergent is coated on the plate with an area concentration of 20 to 130 ng/mm$^2$.

In some other examples, the staining reagent is coated on one of the plate or both plates. The cell separation reagent is coated on one of the plate or both plates. The cell lysing reagent is coated on one of the plate or both plates.

When measuring and analyzing whole blood sample using such device, comprising following steps:
 (a) obtaining a whole blood sample (can be finger prick fresh blood or K$_2$EDTA venous whole blood) and a device;
 (b) depositing the sample on one or both of the plates when the plates are configured in the open configuration,
 (c) after (b), forcing the two plates into a closed configuration; and
 (d) illuminating the light on the device and capturing images of sample in the device while the plates are the closed configuration; and
 (e) analyzing the images to analyze complete blood count in the device.

Figure 8:
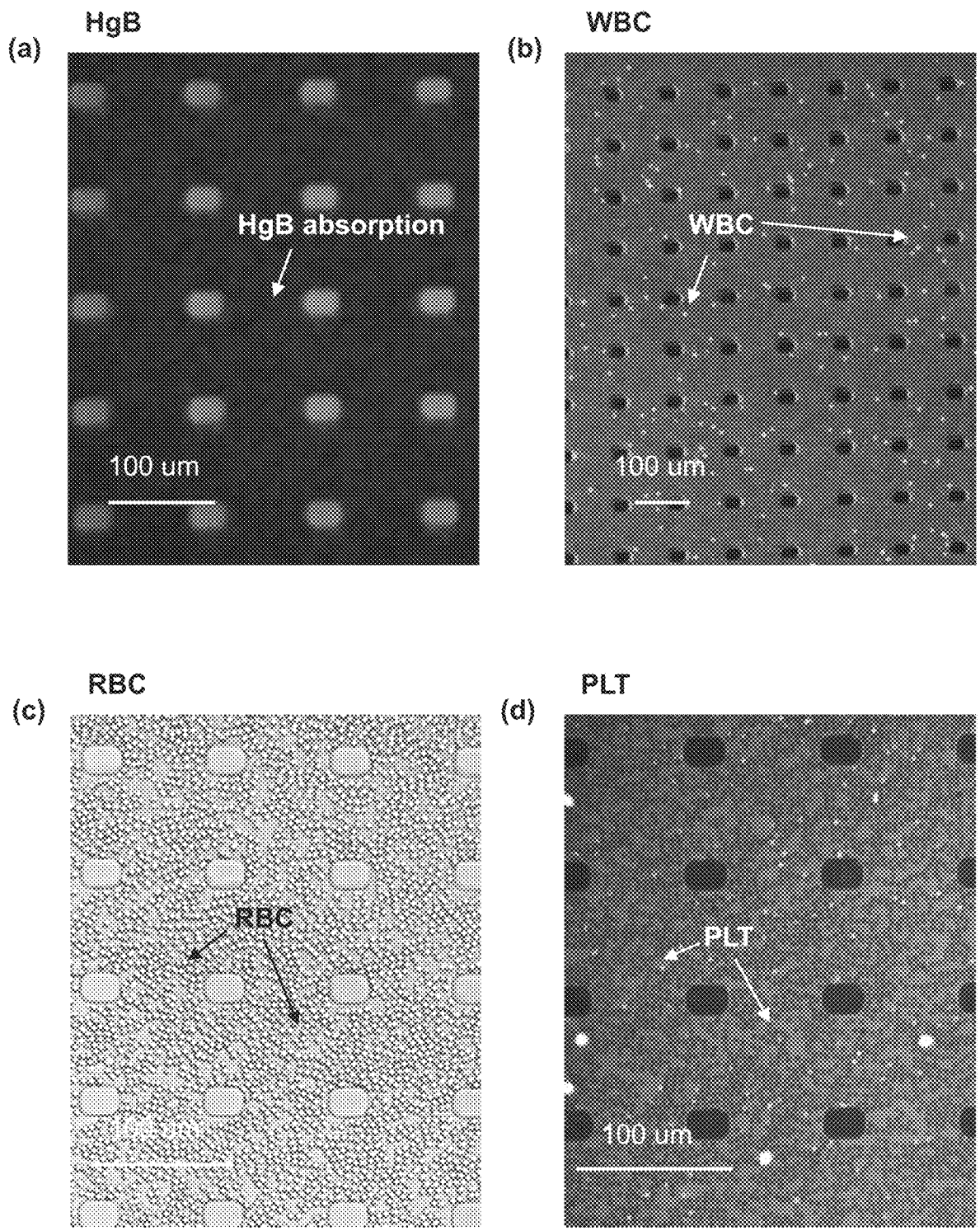
FIG. 8 shows (a) the bright field image of HgB in device at wavelength around 520 nm, (b) fluoresce field image of WBC in device at excitation around 490 nm and emission over 500 nm, (c) the bright field image of RBC in device, (d) fluoresce field image of WBC and PLT in device at excitation around 490 nm and emission over 500 nm, with whole blood inside taken by iphone based optical system.

FIG. 8 shows (a) the bright field image of HgB in device at wavelength around 520 nm, (b) fluoresce field image of WBC in device at excitation around 490 nm and emission over 500 nm, (c) the bright field image of RBC in device, (d) fluoresce field image of WBC and PLT in device at excitation around 490 nm and emission over 500 nm, with whole blood inside taken by iPhone based optical system.

The red blood cell in (a) with pillar height 30 um become multilayers, thus good for HgB measurement. The red blood cell in (c) with a pillar height 5 um become a monolayer and countable in the zoom-in image.

The white blood cell and platelet is stained with AO dye and is bright dots in the fluorescence image. The white blood cell in both 5 um and 30 um spacing device become a monolayer and countable in the zoom-in image. The platelet in 5 um spacing device is a monolayer and countable in the zoom-in image.

Whole blood samples (venous in K2EDTA tube) from 50 to 100 patients are measured by QMAX device and compared with commercial hemocytometer as Horiba Pentra 60C. 9 uL whole blood was dropped onto plate 2, and pressed by plate 1. The card is then read by smartphone based optical system as shown in FIG. 8. The cells are counted by local software using both OpenCV and machine learning algorithm.

Figure 9:
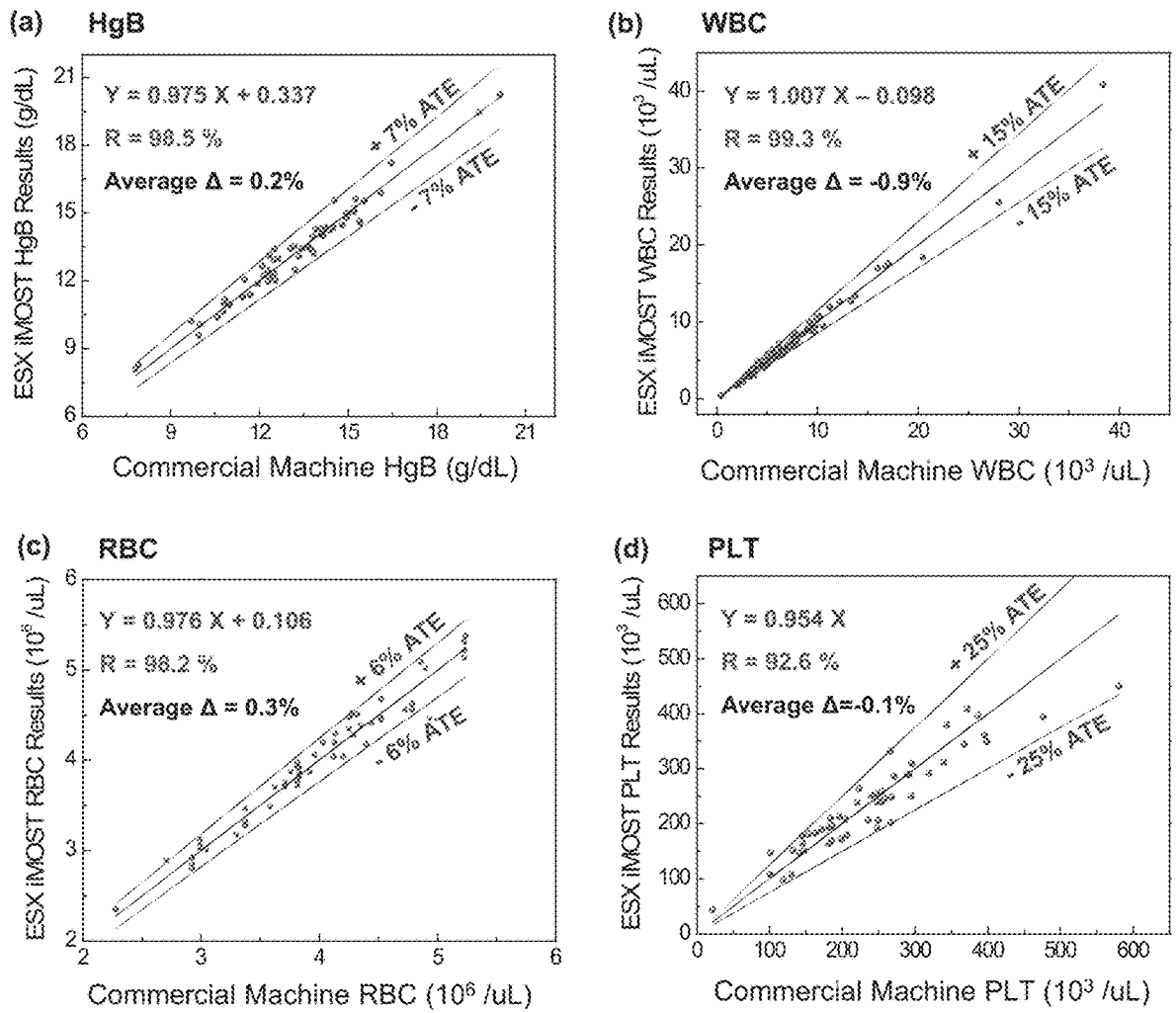
FIG. 9 shows the example HgB, WBC, RBC, PLT analyze results of whole blood samples using QMAX device and compared with commercial hemocytometer as Horiba Pentra 60C. The results show good accuracy of the device and method compared with commercial machine.

FIG. 9 shows the example HgB, WBC, RBC, PLT analyze results of whole blood samples using QMAX device and compared with commercial hemocytometer as Horiba Pentra 60C. The results show good accuracy of the device and method compared with commercial machine.

In details, compared with Horiba Pentra 60C, the HgB reading has R2=98.5% with commercial machine over measured range of 7 g/dL to 20 g/dL, the WBC reading has R2=99.3% with commercial machine over measured range of 0.4×10$^3$/uL to 38×10$^3$/uL, the RBC reading has R2=98.2% with commercial machine over measured range of 2.3×10$^6$/uL to 5.2×10$^6$/uL, the WBC reading has R2=93% with commercial machine over measured range of 21×10$^3$/uL to 581×10$^3$/uL.

Example 2 QMAX Device Measure WBC and WBC Differentiate

Figure 10:
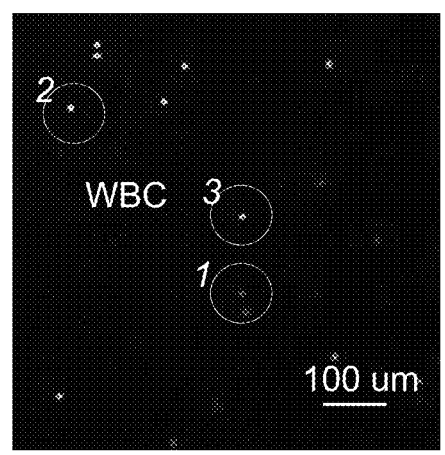
FIG. 10 shows (a) the fluorescence photo taken by smartphone optical system of WBCs in one QMAX device and (b) the statistic counting summary of WBCs in the device, plotting WBC count vs. Green channel intensity over red channel intensity of each WBC.
Figure 10:
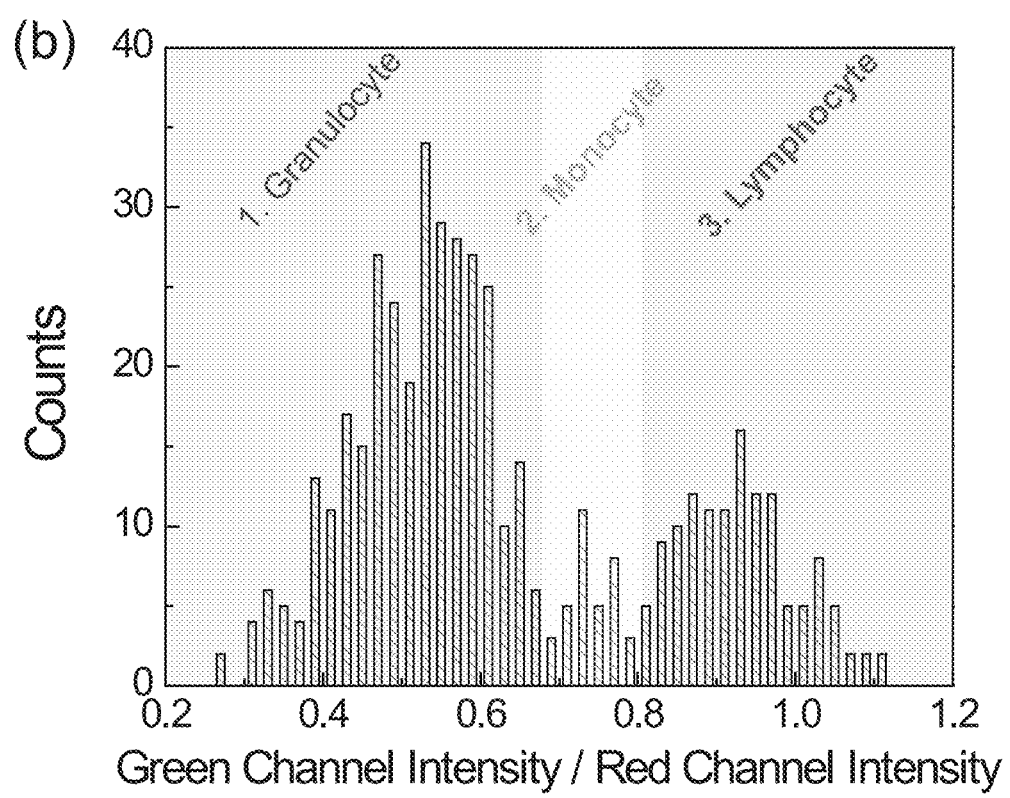

One example result using QMAX device to measure WBC and WBC differentiate is shown in FIG. 10. The device is able to measure all the WBC and three sub-types (granulocyte, monocyte, lymphocyte) without dilution. The preliminary test shows the results using such device is accurate compared with commercial machine.

FIG. 10 shows the (a) the fluorescence photo take by smartphone optical system of WBCs in one QMAX device and (b) the statistic counting summary of WBCs in the device, plotting WBC count vs. Green channel intensity over red channel intensity of each WBC.

The device was same as the WBC device in example-1.

The acridine orange dye for staining WBC was coated on the plate 1. When binding to DNA, AO intercalates with DNA as a monomer and yields intense green fluorescence under blue excitation. When binding to RNA and proteins it forms an electrostatic complex in a polymeric form that yields red fluorescence under blue excitation. Since the three sub-types (granulocyte, monocyte, lymphocyte) have different DNA/RNA ratio, by analyzing the green and red fluorescence ratio of each WBC, the WBC differentiate can be achieved.

The acridine orange was coated on the plate with an area concentration of 10 to 80 $ng/mm^2$ and Zwittergent was coated on the plate with an area concentration of 20 to 130 $ng/mm^2$.

When measuring and analyzing whole blood sample using such device, comprising following steps:
(a) obtaining a whole blood sample (can be finger prick fresh blood or $K_2$EDTA venous whole blood) and a device;
(b) depositing the sample on one or both of the plates when the plates are configured in the open configuration,
(c) after (b), forcing the two plates into a closed configuration; and
(d) illuminating the light on the device and capturing images of sample in the device while the plates are the closed configuration; and
(e) analyzing the images to analyze complete blood count in the device.

The excitation illumination is at the wavelength 450 nm to 480 nm, the emission is long pass with cut off at around 520 nm, thus both green (550 nm) and red color (650 nm) fluorescence of each WBC can be observed from camera.

From the result, the white blood cell is stained with AO dye and is colorful dots in the fluorescence image with clearly three color (green, yellow and red) as shown in FIG. 10(a), which corresponding to lymphocyte (more DNA), monocyte (balance DNA, RNA) and granulocyte (more RNA). The color of each WBC was analyzed with machine learning and software, and distinguished into 3 clusters as shown in FIG. 10(b).

iMOST HgB+WBC+WBC Differentiate QMAX Card Example:

The spacer height, the spacing between the plates, and/or sample thickness is around 30 um.
The spacer height, the spacing between the plates, and/or sample thickness is 20 um to 40 um.
The spacer is rectangle shape with round corners.
The lateral dimension of a spacer is around 30 μm by 40 um.
The lateral dimension of a spacer is 10 um to 40 um.
The round corners of spacer has a diameter of 10 um.
The spacer is in a rectangular lattice array.
The inter-spacer spacing of spacers is around 80 μm.
The inter-spacer spacing of spacers is 70 μm to 150 um.
The length of one plate of Q-Card is 27 mm and the width of this plate is 22 mm.
The length of one plate is Q-Card is 32 mm and the width of this plate is 24 mm.
The area of one plate is around 600 $mm^2$ and the area of another plate is around 750 $mm^2$.
The thickness of one plate of Q-Card is around 175 um.
The thickness of one plate of Q-Card is around 1 mm.
The area of the notch on the QMAX card is in the range of 10 to 30 $mm^2$.
The notch is half-round shape with a diameter of 3 to 6 mm.
The notch has a width of 3 mm and a length of 6 mm.
The width of the hinge joint is around 6 mm.
The length of the hinge joint is around 20 mm.
The hinge has a thickness around 70 μm.
The reagent is coated by droplet printing into an array.
The reagent is coated by spray.
The acridine orange or other staining reagents is coated onto the first plate, or the second plate or both.
The Zwittergent or other detergent is coated onto the first plate, or the second plate or both.
The acridine orange is coated on the plate with an area concentration of 10 to 60 $ng/mm^2$ and Zwittergent is coated on the plate with an area concentration of 20 to 130 $ng/mm^2$.
The material of first place and second plate is Poly(methyl methacrylate).
A landing mark for blood droplet is on the outside surface of first plate or second plate.
A landing mark for blood droplet is a small dot or a small cross.
A landing mark for blood droplet is outside the field of view of the image.
A landing mark for blood droplet is near the center of the card.
At least one of the plates is transparent.

iMOST RBC+PLT QMAX card example:
Same as above 1, except:
The spacer height, the spacing between the plates, and/or sample thickness is around 5 um.
The spacer height, the spacing between the plates, and/or sample thickness is 2 um to 7 um.
The lateral dimension of a spacer is around 30 μm by 40 um.
The lateral dimension of a spacer is 5 um to 40 um.
The acridine orange or other staining reagents is coated onto the first plate, or the second plate or both.
The Zwittergent or other detergent is coated onto the first plate, or the second plate or both.
The acridine orange is coated on the plate with an area concentration of 10 to 60 $ng/mm^2$ and Zwittergen is coated on the plate with an area concentration of 20 to 130 $ng/mm^2$.

The invention claimed is:
1. An adapter device for analyzing an analyte in a liquid sample, comprising:
(a) an attachment member configured to attach the adapter device to an apparatus that comprises a light source and a camera;
(b) a card slot configured to accommodate a sample card, which contains a liquid sample that is compressed into a layer of uniform thickness, wherein when the sample card inserted into the card slot, the sample is positioned under the view of the camera and the light source;

(c) the light source forms a first beam with a specific wavelength range, wherein a part of the first beam illuminates on the edge of the sample card and travels in the sample card to illuminate the sample;

(d) a mirror configured to deflect part of the first beam to form a second beam that back-illuminates the sample in an oblique angle; and (e) an absorber configured to absorb at least a part of the first beam that is not deflected by the mirror.

2. The device of claim 1, wherein the adapter comprises a bandpass excitation filter with a transmission band from 450 nm to 480 nm.

3. The device of claim 1, wherein the adapter device comprises a long pass emission filter with cut-on wavelength between 510 nm and 525 nm.

4. The device of claim 1, wherein the adapter device comprises an excitation light illumination with an oblique angle larger than the collection angle of the camera of the apparatus which the adapter device attaches to.

5. The device of claim 1, wherein the adapter device comprises a lens including a focus distance between 2 mm and 6 mm that enables the camera to image the sample inserted into the adapter device.

6. The device of claim 1, wherein the adapter device comprises a bandpass filter with transmission band from 520 nm to 580 nm.

7. The device of claim 1, wherein the adapter device comprises a light illumination angle 85 degree to 95 degree relative to the surface of the sample.

8. The device of claim 1, wherein the adapter device comprises a lens including a focus distance between 2 mm and 4 mm that enables the camera to image the sample inserted into the adapter device.

9. The device of claim 1, wherein the average thickness of the layer of uniform thickness is in the range of 2.0 um to 7.5 um.

10. The device of claim 1, wherein the average thickness of the layer of uniform thickness is in the range of 7.5 um to 10.5 um.

11. The device of claim 1, wherein the average thickness of the layer of uniform thickness is in the range of 9.5 um to 12.5 um.

12. The device of claim 1, wherein the average thickness of the layer of uniform thickness is in the range of 9.5 um to 12.5 um.

13. The device of claim 1, wherein the average thickness of the layer of uniform thickness is in the range of 11.5 um to 13.5 um.

14. The device of claim 1, wherein the average thickness of the layer of uniform thickness is in the range of 12.5 um to 14.5 um.

15. The device of claim 1, wherein the average thickness of the layer of uniform thickness is in the range of 13.5 um to 16 um.

16. A method for analyzing an analyte in a liquid sample, comprising:

(a) obtaining the liquid sample;

(b) compressing at least part of the sample into a layer of uniform thickness with a sample card, (c) inserting the sample card into an adaptor device, which is configured to be attached to an apparatus that comprises a light source and a camera;

(d) illuminating the sample with light from the light source, wherein
  i. the light forms a first beam with a specific wavelength range, part of the first beam illuminating on the edge of the sample card and travels in the sample card to illuminate the sample;
  ii. part of the first beam is deflected by a mirror of the adapter device to form a second beam that back-illuminates the sample in an oblique angle; and
  iii. at least a part of the first beam that is not deflected by the mirror is absorbed by an absorber of the adapter device.

17. The method of claim 16, wherein the adapter device comprises a bandpass excitation filter with a transmission band from 450 nm to 480 nm.

18. The method of claim 16, wherein the adapter device comprises a long pass emission filter with cut-on wavelength between 510 nm and 525 nm.

19. The device of claim 16, wherein the adapter device comprises an excitation light illumination with an oblique angle larger than the collection angle of the camera of the apparatus which the adapter device attaches to.

20. The method of claim 16, wherein the adapter device comprises a lens including a focus distance between 2 mm and 6 mm.

21. The method of claim 16, wherein the adapter device comprises a bandpass filter with transmission band from 520 nm to 580 nm.

22. The method of claim 16, wherein the adapter device comprises a light illumination angle 85 degree to 95 degree relative to the surface of the sample.

23. The method of claim 16, wherein the adapter device comprises a lens including a focus distance between 2 mm and 4 mm.

24. The method of claim 16, wherein the average thickness of the layer of uniform thickness is in the range of 2.0 um to 7.5 um.

25. The method of claim 16, wherein the average thickness of the layer of uniform thickness is in the range of 7.5 um to 10.5 um.

26. The method of claim 16, wherein the average thickness of the layer of uniform thickness is in the range of 9.5 um to 12.5 um.

27. The method of claim 16, wherein the average thickness of the layer of uniform thickness is in the range of 9.5 um to 12.5 um.

28. The method of claim 16, wherein the average thickness of the layer of uniform thickness is in the range of 11.5 um to 13.5 um.

29. The method of claim 16, wherein the average thickness of the layer of uniform thickness is in the range of 12.5 um to 14.5 um.

30. The method of claim 16, wherein the average thickness of the layer of uniform thickness is in the range of 13.5 um to 16 um.

* * * * *